United States Patent [19]
Amara et al.

[11] Patent Number: 5,882,926
[45] Date of Patent: Mar. 16, 1999

[54] EXCITATORY AMINO ACID TRANSPORTER GENE AND USES

[75] Inventors: Susan G. Amara, Portland, Oreg.; Jeffrey L. Arriza, Kennett Square, Pa.; Scott Eliasof; Michael P. Kavanaugh, both of Portland, Oreg.

[73] Assignee: Oregon Health Sciences University, Portland, Oreg.

[21] Appl. No.: 948,569

[22] Filed: Oct. 10, 1997

Related U.S. Application Data

[60] Provisional application No. 60/028,325 Oct. 11, 1996.

[63] Continuation-in-part of Ser. No. 140,729, Oct. 20, 1993, Pat. No. 5,658,782.

[51] Int. Cl.[6] .............................. C12N 5/00; C12N 15/00; C07K 1/00; C07H 21/04

[52] U.S. Cl. .......................... 435/325; 435/6; 435/320.1; 435/361; 435/364; 435/365; 435/367; 435/369; 530/350; 536/23.5; 536/24.31

[58] Field of Search ........................... 435/6, 320.1, 325, 435/361, 364, 365, 367, 369; 530/350; 536/23.5, 24.31

[56] References Cited

U.S. PATENT DOCUMENTS

| | | | |
|---|---|---|---|
| 4,683,195 | 7/1987 | Mullins et al. | 435/6 |
| 4,683,202 | 11/1990 | Mullins | 435/91 |
| 5,385,831 | 1/1995 | Mulvihill et al. | 435/69.1 |
| 5,424,185 | 6/1995 | Lam et al. | 435/6 |

OTHER PUBLICATIONS

Arriza et al. (1994) J. Neurosci., vol. 14, No. 9, pp. 5559–5569.
Kanai et al. (1992) Nature, 360: 467–471.
Kanai et al. (1993) Trends in Neurosci., vol. 16, No. 9, pp. 365–370.
Kanai et al., (1993) FASEB J., 7: 1450–1459.
Kanner, (1993), FEBS Lett., 325 (1,2): pp. 95–99.
Pines et al., (1992) Nature, 360: pp. 464–467.
Schloss et al. (1992) FEBS Lett. 307 (1): pp. 76–80.
Shashidharan et al., (1993), Biochim. Biophys. Acta., 1216: pp. 161–164.
Stelzner et al., (1993) FASEB J., 7(4/part2): A575.
Storck et al., (1992), Proc. Natl. Acad. Sci., 89: pp. 10955–10959.
Uhl, (1992), Trends in Neurosci., 15(7): 265–268.
Anderson et al., (1989) J. Biol. Chem., 264: pp. 8222–822.
Arriza et al., (1992) J. Neurosci., 12: 4045–4055.
Barish, (1983) J. Physiol., 342: 309–325.
Bertling et al., (1987) Bioscience Reports, 7: 107–112.
Blakely et al., (1991) Anal. Biochem., 194: 302–308.
Bouvier et al., (1992) Nature, 360: 471–474.
Bussolati et al., (1992) J. Biol. Chem., 267: 8330–8335.
Choi et al., (1987) Neurosci., 7: 357–358.
Chomczynski & Sacchi, (1987) Anal. Biochem., 162: 156–159.
Christensen (1990), Physiol. Rev., 70: 43: 77.
Christensen et al., (1967), J. Biol. Chem., 242: 5237–5246.
Eisenberg et al., (1984), J. Molec. Biol., 179: 125–142.
Engelke et al., (1992) J. Bacteriol., 171: 5551–5560.
Fairman, (1995) Human Excitatory Amino Acid Transporter 4. Genbank Accession Number U18244.
Felgner et al., (1987) Proc. Natl. Acad. Sci., 84: 7412–7417.
Gesogiou, (1988) AICHE Journal, vol. 34, No. 8, pp. 1233–1248.
Gluzman, (1981) Cell, 23: 175–182.
Guastella et al., (1992) Proc. Natl. Sci., 89: 7189–7193.
Guastella et al., (1990) Science, 249: 1303–1306.
Kanai et al., (1994) J. Biol. Chem., vol. 269, No. 32, pp. 20599–20606.
Kanner & Schuldiner, (1987), CRC Crit. Rev. Biochem., 22: 1–38.
Kavanaugh et al., (1992) J. Biol. Chem., 267: 22007–22009.
Kim et al., (1991) Nature, 352: 725–728.
Kong et al., (1993) J. Biol. Chem., 268: 1509–1512.
Kozak, (1987) Nucleic Acid Res., 15: 8125–8132.
Maenz et al., (1992), J. Biol. Chem., 267: 1510–1516.
Makowske & Christensen, (1982) J. Biol. Chem., 257: 14635–14638.
Nicholls & Atwell, (1990), TIPS, 11: 462–468.
Olney et al., (1990) Science, 248: 596–599.
Quick and Lester, (1994) Methods in Neuroscience, 19: 261–279.
Saiki et al., (1988) Science, 239: 487–491.
Sanger et al., (1977) Proc. Natl. Acad. Sci., 74: 5463.
Smith & Johnson, (1988) Gene, 67: 31–40.
Smithies et al., (1985) Nature, 317: 230–234.
Thomas & Capecchi, (1987) Cell, 51: 503–512.
Wallace et al., (1990) J. Bacteriol., 172: 3214–3220.
Wang et al., (1991) Nature, 352: 729–731.
Dreyer et al., (1996) Arch. Ophthalmol., 114: 299–305.
Honda, (1996) Nippon Ganka Gakkst Zasshi, 100: 937–955.
Kalloniatis, (1995) J. Amer. Optom. Assoc., 66: 750–757.
Zerangue et al., (1995) J. Biol. Chem., 270: 6433–6435.
Kataoka et al., (1997) J. Neurosci., 17: 7017–7024.
Sheng et al., (1996) Neuron., 17: 575–578.

*Primary Examiner*—Rebecca E. Prouty
*Assistant Examiner*—Lisa J. Hobbs
*Attorney, Agent, or Firm*—McDonnell Boehnen Hulbert & Berghoff

[57] ABSTRACT

This invention relates to novel mammalian excitatory amino acid transporter proteins and genes encoding such proteins. The invention is directed towards the isolation, characterization and use of human excitatory amino acid transporter proteins for pharmacological screening of analogues, agonists, antagonists, inhibitors, modulators and facilitators of excitatory amino acid transport in a variety of tissues, particularly neuronal tissues. This invention provides isolated nucleic acid encoding a novel excitatory amino acid transporter subtype that is specifically expressed in retina. Also provided are recombinant expression constructs capable of expressing this novel transporter in transformed prokaryotic and eukaryotic cells, and also provides such transformed cell cultures producing the novel human transporter. Purified transporter protein and membranes comprising the transporter protein are also provided. The invention provides methods of screening compounds in vitro for transporter binding properties using said preparations of protein and membranes from transformed cell cultures, as well as from amphibian oocytes expressing the human transporter protein provided herein.

11 Claims, 7 Drawing Sheets

Figure 1A

```
          10        20        30        40        50        60
           *         *         *         *         *         *
GAATTCGCCGTGTGGCCGCCTTAGAGGGAAGCCACACGGGCATGGCCGTGGGGCTGGCGA 70        80        90       100       110       120
           *         *         *         *         *         *
CTGGTGTTTAGCAACTCCGACCACCTGCCTGCTGAGGGGCTAGAGCCCTCAGCCCAGACC 130       140       150       160       170       180
           *         *         *         *         *         *
CTGTGCCCCCGGCCGGGCTCTCATGCGTGGAATGGTGCTGTGCCCCTTGCCAGCAGGCCA 190       200       210       220       230       240
           *         *         *         *         *         *
GGCTCACCATGGTGCCGCATACCATCTTGGCACGGGGGAGGGACGTGTGCAGGCGGAATG
           MetValProHisThrIleLeuAlaArgGlyArgAspValCysArgArgAsn>

250       260       270       280       290       300
           *         *         *         *         *         *
GACTCCTCATCCTGTCTGTGCTGTCTGTCATCGTGGGCTGCCTCCTCGGCTTCTTCTTGA
GlyLeuLeuIleLeuSerValLeuSerValIleValGlyCysLeuLeuGlyPhePheLeu>

310       320       330       340       350       360
           *         *         *         *         *         *
GGACCCGGCGCCTCTCACCACAGGAAATTAGTTACTTCCAGTTCCCCGGAGAGCTCCTGA
ArgThrArgArgLeuSerProGlnGluIleSerTyrPheGlnPheProGlyGluLeuLeu>

370       380       390       400       410       420
           *         *         *         *         *         *
TGAGGATGCTGAAGATGATGATCCTGCCACTGGTGTTCTCCAGCTTGATGTCCGGACTTG
MetArgMetLeuLysMetMetIleLeuProLeuValPheSerSerLeuMetSerGlyLeu>

430       440       450       460       470       480
           *         *         *         *         *         *
CCTCCCTGGATGCCAAGACCTCTAGCCGCCTGGGCGTCCTCACCGTGGCGTACTACCTGT
AlaSerLeuAspAlaLysThrSerSerArgLeuGlyValLeuThrValAlaTyrTyrLeu>

490       500       510       520       530       540
           *         *         *         *         *         *
GGACCACCTTCATGGCTGTCATCGTGGGCATCTTCATGGTCTCCATCATCCACCCAGGCA
TrpThrThrPheMetAlaValIleValGlyIlePheMetValSerIleIleHisProGly>

550       560       570       580       590       600
           *         *         *         *         *         *
GCGCGGCCCAGAAGGAGACCACGGAGCAGAGTGGGAAGCCCATCATGAGCTCAGCCGATG
SerAlaAlaGlnLysGluThrThrGluGlnSerGlyLysProIleMetSerSerAlaAsp>

610       620       630       640       650       660
           *         *         *         *         *         *
CCCTGTTGGACCTCATCCGGAACATGTTCCCAGCCAACCTAGTAGAAGCCACATTCAAAC
AlaLeuLeuAspLeuIleArgAsnMetPheProAlaAsnLeuValGluAlaThrPheLys>

670       680       690       700       710       720
           *         *         *         *         *         *
AGTACCGCACCAAGACCACCCCAGTTGTCAAGTCCCCCAAGGTGGCACCAGAGGAGGCCC
GlnTyrArgThrLysThrThrProValValLysSerProLysValAlaProGluGluAla>

730       740       750       760       770       780
           *         *         *         *         *         *
CTCCTCGGCGGATCCTCATCTACGGGGTCCAGGAGGAGAATGGCTCCCATGTGCAGAACT
ProProArgArgIleLeuIleTyrGlyValGlnGluGluAsnGlySerHisValGlnAsn>
```

Figure 1B

```
            790       800       810       820       830       840
              *         *         *         *         *         *
       TCGCCCTGGACCTGACCCCGCCGCCCGAGGTCGTTTACAAGTCAGAGCCGGGCACCAGCG
       PheAlaLeuAspLeuThrProProProGluValValTyrLysSerGluProGlyThrSer>

850       860       870       880       890       900
              *         *         *         *         *         *
       ATGGCATGAATGTGCTGGGCATCGTCTTCTTCTCTGCCACCATGGGCATCATGCTGGGCC
       AspGlyMetAsnValLeuGlyIleValPhePheSerAlaThrMetGlyIleMetLeuGly>

910       920       930       940       950       960
              *         *         *         *         *         *
       GCATGGGTGACAGCGGGGGCCCCCTGGTCAGCTTCTGCCAGTGCCTCAATGAGTCGGTCA
       ArgMetGlyAspSerGlyGlyProLeuValSerPheCysGlnCysLeuAsnGluSerVal>

970       980       990      1000      1010      1020
              *         *         *         *         *         *
       TGAAGATCGTGGCGGTGGCTGTGTGGTATTTCCCCTTCGGCATTGTGTTCCTCATTGCGG
       MetLysIleValAlaValAlaValTrpTyrPheProPheGlyIleValPheLeuIleAla>

1030      1040      1050      1060      1070      1080
              *         *         *         *         *         *
       GTAAGATCCTGGAGATGGACGACCCCAGGGCCGTCGGCAAGAAGCTGGGCTTCTACTCAG
       GlyLysIleLeuGluMetAspAspProArgAlaValGlyLysLysLeuGlyPheTyrSer>

1090      1100      1110      1120      1130      1140
              *         *         *         *         *         *
       TCACCGTGGTGTGCGGGCTGGTGCTCCACGGGCTCTTTATCCTGCCCCTGCTCTACTTCT
       ValThrValValCysGlyLeuValLeuHisGlyLeuPheIleLeuProLeuLeuTyrPhe>

1150      1160      1170      1180      1190      1200
              *         *         *         *         *         *
       TCATCACCAAGAAGAATCCCATCGTCTTCATCCGCGGCATCCTGCAGGCTCTGCTCATCG
       PheIleThrLysLysAsnProIleValPheIleArgGlyIleLeuGlnAlaLeuLeuIle>

1210      1220      1230      1240      1250      1260
              *         *         *         *         *         *
       CGCTGGCCACCTCCTCCAGCTCAGCCACACTGCCCATCACCTTCAAGTGCCTGCTGGAGA
       AlaLeuAlaThrSerSerSerSerAlaThrLeuProIleThrPheLysCysLeuLeuGlu>

1270      1280      1290      1300      1310      1320
              *         *         *         *         *         *
       ACAACCACATCGACCGGCGCATCGCTCGCTTCGTGCTGCCCGTGGGTGCCACCATCAACA
       AsnAsnHisIleAspArgArgIleAlaArgPheValLeuProValGlyAlaThrIleAsn>

1330      1340      1350      1360      1370      1380
              *         *         *         *         *         *
       TGGACGGCACTGCGCTCTACGAGGCTGTGGCCGCCATCTTCATCGCCCAGGTCAACAACT
       MetAspGlyThrAlaLeuTyrGluAlaValAlaAlaIlePheIleAlaGlnValAsnAsn>

1390      1400      1410      1420      1430      1440
              *         *         *         *         *         *
       ACGAGCTGGACTTTGGCCAGATCATCACCATCAGTATCACAGGCACTGCAGCCAGCATTG
       TyrGluLeuAspPheGlyGlnIleIleThrIleSerIleThrGlyThrAlaAlaSerIle>

1450      1460      1470      1480      1490      1500
              *         *         *         *         *         *
       GGGCAGCTGGCATCCCCCAGGCCGGCCTCGTCACCATGGTCATCGTGCTCACCTCCGTGG
       GlyAlaAlaGlyIleProGlnAlaGlyLeuValThrMetValIleValLeuThrSerVal>
```

Figure 1C

```
         1510       1520       1530       1540       1550       1560
           *          *          *          *          *          *
      GACTGCCCACCGATGACATCACCCTCATCATTGGCGTTGACTGGGCTCTGGACCGTTTCC
      GlyLeuProThrAspAspIleThrLeuIleIleGlyValAspTrpAlaLeuAspArgPhe>

1570       1580       1590       1600       1610       1620
           *          *          *          *          *          *
      GCACCATGATTAACGTGCTGGGTGATGCGCTGGCAGCGGGGATCATGGCCCATATATGTC
      ArgThrMetIleAsnValLeuGlyAspAlaLeuAlaAlaGlyIleMetAlaHisIleCys>

1630       1640       1650       1660       1670       1680
           *          *          *          *          *          *
      GGAAGGATTTTGCCCGGGACACAGGCACCGAGAAACTGCTGCCCTGCGAGACCAAGCCAG
      ArgLysAspPheAlaArgAspThrGlyThrGluLysLeuLeuProCysGluThrLysPro>

1690       1700       1710       1720       1730       1740
           *          *          *          *          *          *
      TGAGCCTCCAGGAGATCGTGGCAGCCCAGCAGAATGGCTGTGTGAAGAGTGTAGCCGAGG
      ValSerLeuGlnGluIleValAlaAlaGlnGlnAsnGlyCysValLysSerValAlaGlu>

1750       1760       1770       1780       1790       1800
           *          *          *          *          *          *
      CCTCCGAGCTCACCCTGGGCCCCACCTGCCCCCACCACGTCCCCGTTCAAGTGGAGCGGG
      AlaSerGluLeuThrLeuGlyProThrCysProHisHisValProValGlnValGluArg>

1810       1820       1830       1840       1850       1860
           *          *          *          *          *          *
      ATGAGGAGCTGCCCGCTGCGAGTCTGAACCACTGCACCATCCAGATCAGCGAGCTGGAGA
      AspGluGluLeuProAlaAlaSerLeuAsnHisCysThrIleGlnIleSerGluLeuGlu>

1870       1880       1890       1900       1910       1920
           *          *          *          *          *          *
      CCAATGTCTGAGCCTGCGGAGCTGCAGGGGCAGGCGAGGCCTCCAGGGGCAGGGTCCTGA
      ThrAsnVal***>

1930       1940       1950       1960       1970       1980
           *          *          *          *          *          *
      GGCAGGAACTCGACTCTCCAACCCTCCTGAGCAGCCGGTAGGGGGCAGGATCACACATTC 1990       2000       2010       2020       2030       2040
           *          *          *          *          *          *
      TTCTCACCCTTGAGAGGNTGGAATTAACCCCGCTTGGACGGAAAATGTNTCTCAAGAGAA 2050       2060       2070       2080       2090       2100
           *          *          *          *          *          *
      GGGAAAGGNTGCATGGGGGAGCCCATCCAGGGAGTGATGGGCCCGGATTGGCTGANGGCC 2110       2120       2130       2140       2150       2160
           *          *          *          *          *          *
      CNTTGTGAAAGTTTCCCCCGTNGTGAACCCCGGTGAAGGGGGGAAGGCAGGGGGTTTTCC 2170       2180       2190
           *          *          *
      GGCCCCCCTTTTCTTGGATGANAGGATTTGGACC
```

Figure 2

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1656

( x i ) SEQUENCE DESCRIPTION: SEQ ID NO:1:

```
AAAGAAGAGA  CCCTCCTAGA  AAAGTAAAAT  ATG  ACT  AAA  AGC  AAT  GGA  GAA  GAG         5 4
                                    Met  Thr  Lys  Ser  Asn  Gly  Glu  Glu
                                     1                    5

CCC  AAG  ATG  GGG  GGC  AGG  ATG  GAG  AGA  TTC  CAG  CAG  GGA  GTC  CGT  AAA    1 0 2
Pro  Lys  Met  Gly  Gly  Arg  Met  Glu  Arg  Phe  Gln  Gln  Gly  Val  Arg  Lys
     1 0                     1 5                      2 0
```

-continued

| | | | | | | | | | | | | | | | | |
|---|---|---|---|---|---|---|---|---|---|---|---|---|---|---|---|---|
| CGC | ACA | CTT | TTG | GCC | AAG | AAG | AAA | GTG | CAG | AAC | ATT | ACA | AAG | GAG | GTT | 150 |
| Arg | Thr | Leu | Leu | Ala | Lys | Lys | Lys | Val | Gln | Asn | Ile | Thr | Lys | Glu | Val | |
| 25 | | | | 30 | | | | | 35 | | | | | | 40 | |

| GTT | AAA | AGT | TAC | CTG | TTT | CGG | AAT | GCT | TTT | GTG | CTG | CTC | ACA | GTC | ACC | 198 |
|---|---|---|---|---|---|---|---|---|---|---|---|---|---|---|---|---|
| Val | Lys | Ser | Tyr | Leu | Phe | Arg | Asn | Ala | Phe | Val | Leu | Leu | Thr | Val | Thr | |
| | | | | 45 | | | | | 50 | | | | | 55 | | |

| GCT | GTC | ATT | GTG | GGT | ACA | ATC | CTT | GGA | TTT | ACC | CTC | CGA | CCA | TAC | AGA | 246 |
|---|---|---|---|---|---|---|---|---|---|---|---|---|---|---|---|---|
| Ala | Val | Ile | Val | Gly | Thr | Ile | Leu | Gly | Phe | Thr | Leu | Arg | Pro | Tyr | Arg | |
| | | | 60 | | | | 65 | | | | | | 70 | | | |

| ATG | AGC | TAC | CGG | GAA | GTC | AAG | TAC | TTC | TCC | TTT | CCT | GGG | GAA | CTT | CTG | 294 |
|---|---|---|---|---|---|---|---|---|---|---|---|---|---|---|---|---|
| Met | Ser | Tyr | Arg | Glu | Val | Lys | Tyr | Phe | Ser | Phe | Pro | Gly | Glu | Leu | Leu | |
| | | 75 | | | | | 80 | | | | | 85 | | | | |

| ATG | AGG | ATG | TTA | CAG | ATG | CTG | GTC | TTA | CCA | CTT | ATC | ATC | TCC | AGT | CTT | 342 |
|---|---|---|---|---|---|---|---|---|---|---|---|---|---|---|---|---|
| Met | Arg | Met | Leu | Gln | Met | Leu | Val | Leu | Pro | Leu | Ile | Ile | Ser | Ser | Leu | |
| | 90 | | | | | 95 | | | | | 100 | | | | | |

| GTC | ACA | GGA | ATG | GCG | GCG | CTA | GAT | AGT | AAG | GCA | TCA | GGG | AAG | TGG | GAA | 390 |
|---|---|---|---|---|---|---|---|---|---|---|---|---|---|---|---|---|
| Val | Thr | Gly | Met | Ala | Ala | Leu | Asp | Ser | Lys | Ala | Ser | Gly | Lys | Trp | Glu | |
| 105 | | | | | 110 | | | | | 115 | | | | | 120 | |

| TGC | GGA | GCT | GTA | GTC | TAT | TAT | ATG | ACT | ACC | ACC | ATC | ATT | GCT | GTG | GTG | 438 |
|---|---|---|---|---|---|---|---|---|---|---|---|---|---|---|---|---|
| Cys | Gly | Ala | Val | Val | Tyr | Tyr | Met | Thr | Thr | Thr | Ile | Ile | Ala | Val | Val | |
| | | | | 125 | | | | | 130 | | | | | 135 | | |

| ATT | GGC | ATA | ATC | ATT | GTC | ATC | ATC | ATC | CAT | CCT | GGG | AAG | GGC | ACA | AAG | 486 |
|---|---|---|---|---|---|---|---|---|---|---|---|---|---|---|---|---|
| Ile | Gly | Ile | Ile | Ile | Val | Ile | Ile | Ile | His | Pro | Gly | Lys | Gly | Thr | Lys | |
| | | | 140 | | | | | 145 | | | | | 150 | | | |

| GAA | AAC | ATG | CAC | AGA | GAA | GGC | AAA | ATT | GTA | CGA | GTG | ACA | GCT | GCA | GAT | 534 |
|---|---|---|---|---|---|---|---|---|---|---|---|---|---|---|---|---|
| Glu | Asn | Met | His | Arg | Glu | Gly | Lys | Ile | Val | Arg | Val | Thr | Ala | Ala | Asp | |
| | | 155 | | | | | 160 | | | | | 165 | | | | |

| GCC | TTC | CTG | GAC | TTG | ATC | AGG | AAC | ATG | TTA | AAT | CCA | AAT | CTG | GTA | GAA | 582 |
|---|---|---|---|---|---|---|---|---|---|---|---|---|---|---|---|---|
| Ala | Phe | Leu | Asp | Leu | Ile | Arg | Asn | Met | Leu | Asn | Pro | Asn | Leu | Val | Glu | |
| | 170 | | | | | 175 | | | | | 180 | | | | | |

| GCC | TGC | TTT | AAA | CAG | TTT | AAA | ACC | AAC | TAT | GAG | AAG | AGA | AGC | TTT | AAA | 630 |
|---|---|---|---|---|---|---|---|---|---|---|---|---|---|---|---|---|
| Ala | Cys | Phe | Lys | Gln | Phe | Lys | Thr | Asn | Tyr | Glu | Lys | Arg | Ser | Phe | Lys | |
| 185 | | | | | 190 | | | | | 195 | | | | | 200 | |

| GTG | CCC | ATC | CAG | GCC | AAC | GAA | ACG | CTT | GTG | GGT | GCT | GTG | ATA | AAC | AAT | 678 |
|---|---|---|---|---|---|---|---|---|---|---|---|---|---|---|---|---|
| Val | Pro | Ile | Gln | Ala | Asn | Glu | Thr | Leu | Val | Gly | Ala | Val | Ile | Asn | Asn | |
| | | | | 205 | | | | 210 | | | | | 215 | | | |

| GTG | TCT | GAG | GCC | ATG | GAG | ACT | CTT | ACC | CGA | ATC | ACA | GAG | GAG | CTG | GTC | 726 |
|---|---|---|---|---|---|---|---|---|---|---|---|---|---|---|---|---|
| Val | Ser | Glu | Ala | Met | Glu | Thr | Leu | Thr | Arg | Ile | Thr | Glu | Glu | Leu | Val | |
| | | | 220 | | | | | 225 | | | | | 230 | | | |

| CCA | GTT | CCA | GGA | TCT | GTG | AAT | GGA | GTC | AAT | GCC | CTG | GGT | CTA | GTT | GTC | 774 |
|---|---|---|---|---|---|---|---|---|---|---|---|---|---|---|---|---|
| Pro | Val | Pro | Gly | Ser | Val | Asn | Gly | Val | Asn | Ala | Leu | Gly | Leu | Val | Val | |
| | | 235 | | | | | 240 | | | | | 245 | | | | |

| TTC | TCC | ATG | TGC | TTC | GGT | TTT | GTG | ATT | GGA | AAC | ATG | AAG | GAA | CAG | GGG | 822 |
|---|---|---|---|---|---|---|---|---|---|---|---|---|---|---|---|---|
| Phe | Ser | Met | Cys | Phe | Gly | Phe | Val | Ile | Gly | Asn | Met | Lys | Glu | Gln | Gly | |
| | 250 | | | | | 255 | | | | | 260 | | | | | |

| CAG | GCC | CTG | AGA | GAG | TTC | TTT | GAT | TCT | CTT | AAC | GAA | GCC | ATC | ATG | AGA | 870 |
|---|---|---|---|---|---|---|---|---|---|---|---|---|---|---|---|---|
| Gln | Ala | Leu | Arg | Glu | Phe | Phe | Asp | Ser | Leu | Asn | Glu | Ala | Ile | Met | Arg | |
| 265 | | | | | 270 | | | | | 275 | | | | | 280 | |

| CTG | GTA | GCA | GTA | ATA | ATG | TGG | TAT | GCC | CCC | GTG | GGT | ATT | CTC | TTC | CTG | 918 |
|---|---|---|---|---|---|---|---|---|---|---|---|---|---|---|---|---|
| Leu | Val | Ala | Val | Ile | Met | Trp | Tyr | Ala | Pro | Val | Gly | Ile | Leu | Phe | Leu | |
| | | | | 285 | | | | | 290 | | | | | 295 | | |

| ATT | GCT | GGG | AAG | ATT | GTG | GAG | ATG | GAA | GAC | ATG | GGT | GTG | ATT | GGG | GGG | 966 |
|---|---|---|---|---|---|---|---|---|---|---|---|---|---|---|---|---|
| Ile | Ala | Gly | Lys | Ile | Val | Glu | Met | Glu | Asp | Met | Gly | Val | Ile | Gly | Gly | |
| | | | 300 | | | | | 305 | | | | | 310 | | | |

| CAG | CTT | GCC | ATG | TAC | ACC | GAG | ACT | GTC | ATT | GTT | GGC | TTA | CTC | ATT | CAC | 1014 |
|---|---|---|---|---|---|---|---|---|---|---|---|---|---|---|---|---|
| Gln | Leu | Ala | Met | Tyr | Thr | Glu | Thr | Val | Ile | Val | Gly | Leu | Leu | Ile | His | |
| | | 315 | | | | | 320 | | | | | 325 | | | | |

| GCA | GTC | ATC | GTC | TTG | CCA | CTC | CTC | TAC | TTC | TTG | GTA | ACA | CGG | AAA | AAC | 1062 |
|---|---|---|---|---|---|---|---|---|---|---|---|---|---|---|---|---|
| Ala | Val | Ile | Val | Leu | Pro | Leu | Leu | Tyr | Phe | Leu | Val | Thr | Arg | Lys | Asn | |
| | 330 | | | | | 335 | | | | | 340 | | | | | |

-continued

| | | | | | | | | | | | | | | | | |
|---|---|---|---|---|---|---|---|---|---|---|---|---|---|---|---|---|
| CCT | TGG | GTT | TTT | ATT | GGA | GGG | TTG | CTG | CAA | GCA | CTC | ATC | ACC | GCT | CTG | 1110 |
| Pro | Trp | Val | Phe | Ile | Gly | Gly | Leu | Leu | Gln | Ala | Leu | Ile | Thr | Ala | Leu | |
| 345 | | | | 350 | | | | | 355 | | | | | | 360 | |
| GGG | ACC | TCT | TCA | AGT | TCT | GCC | ACC | CTA | CCC | ATC | ACC | TTC | AAG | TGC | CTG | 1158 |
| Gly | Thr | Ser | Ser | Ser | Ser | Ala | Thr | Leu | Pro | Ile | Thr | Phe | Lys | Cys | Leu | |
| | | | | 365 | | | | | 370 | | | | | 375 | | |
| GAA | GAG | AAC | AAT | GGC | GTG | GAC | AAG | CGC | GTC | ACC | AGA | TTC | GTG | CTC | CCC | 1206 |
| Glu | Glu | Asn | Asn | Gly | Val | Asp | Lys | Arg | Val | Thr | Arg | Phe | Val | Leu | Pro | |
| | | | 380 | | | | | 385 | | | | | 390 | | | |
| GTA | GGA | GCC | ACC | ATT | AAC | CTG | GAT | GGG | ACT | GCC | CTC | TAT | GAG | GCT | TTG | 1254 |
| Val | Gly | Ala | Thr | Ile | Asn | Leu | Asp | Gly | Thr | Ala | Leu | Tyr | Glu | Ala | Leu | |
| | | 395 | | | | | 400 | | | | | 405 | | | | |
| GCT | GCC | ATT | TTC | ATT | GCT | CAA | GTT | AAC | AAC | TTT | GAA | CTG | AAC | TTC | GGA | 1302 |
| Ala | Ala | Ile | Phe | Ile | Ala | Gln | Val | Asn | Asn | Phe | Glu | Leu | Asn | Phe | Gly | |
| | 410 | | | | | 415 | | | | | 420 | | | | | |
| CAA | ATT | ATT | ACA | ATC | AGC | ATC | ACA | GCC | ACA | GCT | GCC | AGT | ATT | GGG | GCA | 1350 |
| Gln | Ile | Ile | Thr | Ile | Ser | Ile | Thr | Ala | Thr | Ala | Ala | Ser | Ile | Gly | Ala | |
| 425 | | | | | 430 | | | | | 435 | | | | | 440 | |
| GCT | GGA | ATT | CCT | CAG | GCG | GGC | CTG | GTC | ACT | ATG | GTC | ATT | GTG | CTG | ACA | 1398 |
| Ala | Gly | Ile | Pro | Gln | Ala | Gly | Leu | Val | Thr | Met | Val | Ile | Val | Leu | Thr | |
| | | | | 445 | | | | | 450 | | | | | 455 | | |
| TCT | GTC | GGC | CTG | CCC | ACT | GAC | GAC | ATC | ACG | CTC | ATC | ATC | GCG | GTG | GAC | 1446 |
| Ser | Val | Gly | Leu | Pro | Thr | Asp | Asp | Ile | Thr | Leu | Ile | Ile | Ala | Val | Asp | |
| | | | 460 | | | | | 465 | | | | | 470 | | | |
| TGG | TTC | TTG | GAT | CGC | CTC | CGG | ACC | ACC | ACC | AAC | GTA | CTG | GGA | GAC | TCC | 1494 |
| Trp | Phe | Leu | Asp | Arg | Leu | Arg | Thr | Thr | Thr | Asn | Val | Leu | Gly | Asp | Ser | |
| | | 475 | | | | | 480 | | | | | 485 | | | | |
| CTG | GGA | GCT | GGG | ATT | GTG | GAG | CAC | TTG | TCA | CGA | CAT | GAA | CTG | AAG | AAC | 1542 |
| Leu | Gly | Ala | Gly | Ile | Val | Glu | His | Leu | Ser | Arg | His | Glu | Leu | Lys | Asn | |
| | 490 | | | | | 495 | | | | | 500 | | | | | |
| AGA | GAT | GTT | GAA | ATG | GGT | AAC | TCA | GTG | ATT | GAA | GAG | AAT | GAA | ATG | AAG | 1590 |
| Arg | Asp | Val | Glu | Met | Gly | Asn | Ser | Val | Ile | Glu | Glu | Asn | Glu | Met | Lys | |
| 505 | | | | | 510 | | | | | 515 | | | | | 520 | |
| AAA | CCA | TAT | CAA | CTG | ATT | GCA | CAG | GAC | AAT | GAA | ACT | GAG | AAA | CCC | ATC | 1638 |
| Lys | Pro | Tyr | Gln | Leu | Ile | Ala | Gln | Asp | Asn | Glu | Thr | Glu | Lys | Pro | Ile | |
| | | | | 525 | | | | | 530 | | | | | 535 | | |
| GAC | AGT | GAA | ACC | AAG | ATG | TAGACTAACA | TAAAGAAACA | CTTT | | | | | | | | 1680 |
| Asp | Ser | Glu | Thr | Lys | Met | | | | | | | | | | | |
| | | | 540 | | | | | | | | | | | | | |

(2) INFORMATION FOR SEQ ID NO:2:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Met | Thr | Lys | Ser | Asn | Gly | Glu | Glu | Pro | Lys | Met | Gly | Gly | Arg | Met | Glu |
| 1 | | | | 5 | | | | | 10 | | | | | 15 | |
| Arg | Phe | Gln | Gln | Gly | Val | Arg | Lys | Arg | Thr | Leu | Leu | Ala | Lys | Lys | Lys |
| | | | 20 | | | | | 25 | | | | | 30 | | |
| Val | Gln | Asn | Ile | Thr | Lys | Glu | Val | Val | Lys | Ser | Tyr | Leu | Phe | Arg | Asn |
| | | 35 | | | | | 40 | | | | | 45 | | | |
| Ala | Phe | Val | Leu | Leu | Thr | Val | Thr | Ala | Val | Ile | Val | Gly | Thr | Ile | Leu |
| | 50 | | | | | 55 | | | | | 60 | | | | |
| Gly | Phe | Thr | Leu | Arg | Pro | Tyr | Arg | Met | Ser | Tyr | Arg | Glu | Val | Lys | Tyr |
| 65 | | | | | 70 | | | | | 75 | | | | | 80 |
| Phe | Ser | Phe | Pro | Gly | Glu | Leu | Leu | Met | Arg | Met | Leu | Gln | Met | Leu | Val |

-continued

```
                            85                              90                              95
Leu  Pro  Leu  Ile  Ile  Ser  Ser  Leu  Val  Thr  Gly  Met  Ala  Ala  Leu  Asp
                    100                      105                     110
Ser  Lys  Ala  Ser  Gly  Lys  Trp  Glu  Cys  Gly  Ala  Val  Val  Tyr  Tyr  Met
          115                      120                     125
Thr  Thr  Thr  Ile  Ile  Ala  Val  Val  Ile  Gly  Ile  Ile  Ile  Val  Ile  Ile
     130                     135                     140
Ile  His  Pro  Gly  Lys  Gly  Thr  Lys  Glu  Asn  Met  His  Arg  Glu  Gly  Lys
145                      150                     155                          160
Ile  Val  Arg  Val  Thr  Ala  Ala  Asp  Ala  Phe  Leu  Asp  Leu  Ile  Arg  Asn
                    165                      170                     175
Met  Leu  Asn  Pro  Asn  Leu  Val  Glu  Ala  Cys  Phe  Lys  Gln  Phe  Lys  Thr
               180                      185                     190
Asn  Tyr  Glu  Lys  Arg  Ser  Phe  Lys  Val  Pro  Ile  Gln  Ala  Asn  Glu  Thr
          195                      200                     205
Leu  Val  Gly  Ala  Val  Ile  Asn  Asn  Val  Ser  Glu  Ala  Met  Glu  Thr  Leu
               210                      215                     220
Thr  Arg  Ile  Thr  Glu  Glu  Leu  Val  Pro  Val  Pro  Gly  Ser  Val  Asn  Gly
225                      230                     235                          240
Val  Asn  Ala  Leu  Gly  Leu  Val  Val  Phe  Ser  Met  Cys  Phe  Gly  Phe  Val
                    245                      250                     255
Ile  Gly  Asn  Met  Lys  Glu  Gln  Gly  Gln  Ala  Leu  Arg  Glu  Phe  Phe  Asp
               260                      265                     270
Ser  Leu  Asn  Glu  Ala  Ile  Met  Arg  Leu  Val  Ala  Val  Ile  Met  Trp  Tyr
          275                      280                     285
Ala  Pro  Val  Gly  Ile  Leu  Phe  Leu  Ile  Ala  Gly  Lys  Ile  Val  Glu  Met
     290                     295                     300
Glu  Asp  Met  Gly  Val  Ile  Gly  Gly  Gln  Leu  Ala  Met  Tyr  Thr  Glu  Thr
305                      310                     315                          320
Val  Ile  Val  Gly  Leu  Leu  Ile  His  Ala  Val  Ile  Val  Leu  Pro  Leu  Leu
                    325                      330                     335
Tyr  Phe  Leu  Val  Thr  Arg  Lys  Asn  Pro  Trp  Val  Phe  Ile  Gly  Gly  Leu
               340                      345                     350
Leu  Gln  Ala  Leu  Ile  Thr  Ala  Leu  Gly  Thr  Ser  Ser  Ser  Ala  Thr
          355                      360                     365
Leu  Pro  Ile  Thr  Phe  Lys  Cys  Leu  Glu  Glu  Asn  Asn  Gly  Val  Asp  Lys
     370                     375                     380
Arg  Val  Thr  Arg  Phe  Val  Leu  Pro  Val  Gly  Ala  Thr  Ile  Asn  Leu  Asp
385                      390                     395                          400
Gly  Thr  Ala  Leu  Tyr  Glu  Ala  Leu  Ala  Ala  Ile  Phe  Ile  Ala  Gln  Val
                    405                      410                     415
Asn  Asn  Phe  Glu  Leu  Asn  Phe  Gly  Gln  Ile  Ile  Thr  Ile  Ser  Ile  Thr
               420                      425                     430
Ala  Thr  Ala  Ala  Ser  Ile  Gly  Ala  Ala  Gly  Ile  Pro  Gln  Ala  Gly  Leu
          435                      440                     445
Val  Thr  Met  Val  Ile  Val  Leu  Thr  Ser  Val  Gly  Leu  Pro  Thr  Asp  Asp
     450                     455                     460
Ile  Thr  Leu  Ile  Ile  Ala  Val  Asp  Trp  Phe  Leu  Asp  Arg  Leu  Arg  Thr
465                      470                     475                          480
Thr  Thr  Asn  Val  Leu  Gly  Asp  Ser  Leu  Gly  Ala  Gly  Ile  Val  Glu  His
                    485                      490                     495
Leu  Ser  Arg  His  Glu  Leu  Lys  Asn  Arg  Asp  Val  Glu  Met  Gly  Asn  Ser
               500                      505                     510
```

```
Val  Ile  Glu  Glu  Asn  Glu  Met  Lys  Lys  Pro  Tyr  Gln  Leu  Ile  Ala  Gln
     515                           520                      525

Asp  Asn  Glu  Thr  Glu  Lys  Pro  Ile  Asp  Ser  Glu  Thr  Lys  Met
     530                      535                 540
```

(2) INFORMATION FOR SEQ ID NO:3:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 34..1755

(xi) SEQUENCE DESCRIPTION: SEQ ID NO:3:

```
GATAGTGCTG AAGAGGAGGG GCGTTCCCAG ACC ATG GCA TCT ACG GAA GGT GCC         54
                                    Met Ala Ser Thr Glu Gly Ala
                                                        545

AAC AAT ATG CCC AAG CAG GTG GAA GTG CGA ATG CCA GAC AGT CAT CTT         102
Asn Asn Met Pro Lys Gln Val Glu Val Arg Met Pro Asp Ser His Leu
550             555             560             565

GGC TCA GAG GAA CCC AAG CAC CGG CAC CTG GGC CTG CGC CTG TGT GAC         150
Gly Ser Glu Glu Pro Lys His Arg His Leu Gly Leu Arg Leu Cys Asp
            570             575             580

AAG CTG GGG AAG AAT CTG CTC ACC CTG ACG GTG TTT GGT GTC ACT             198
Lys Leu Gly Lys Asn Leu Leu Leu Thr Leu Thr Val Phe Gly Val Thr
                585             590             595

CTG GGA GCA GTG TGT GGA GGG CTT CTT CGC TTG GCA TCT CCC ATC CAC         246
Leu Gly Ala Val Cys Gly Gly Leu Leu Arg Leu Ala Ser Pro Ile His
        600             605             610

CCT GAT GTG GTT ATG TTA ATA GCC TTC CCA GGG GAT ATA CTC ATG AGG         294
Pro Asp Val Val Met Leu Ile Ala Phe Pro Gly Asp Ile Leu Met Arg
615             620             625

ATG CTA AAA ATG CTC ATT CTG GGT CTA ATC ATC TCC AGC TTA ATC ACA         342
Met Leu Lys Met Leu Ile Leu Gly Leu Ile Ile Ser Ser Leu Ile Thr
630             635             640             645

GGG TTG TCA GGC CTG GAT GCT AAG GCT AGT GGC CGC TTG GGC ACG AGA         390
Gly Leu Ser Gly Leu Asp Ala Lys Ala Ser Gly Arg Leu Gly Thr Arg
            650             655             660

GCC ATG GTG TAT TAC ATG TCC ACG ACC ATC ATT GCT GCA GTA CTG GGG         438
Ala Met Val Tyr Tyr Met Ser Thr Thr Ile Ile Ala Ala Val Leu Gly
            665             670             675

GTC ATT CTG GTC TTG GCT ATC CAT CCA GGC AAT CCC AAG CTC AAG AAG         486
Val Ile Leu Val Leu Ala Ile His Pro Gly Asn Pro Lys Leu Lys Lys
        680             685             690

CAG CTG GGG CCT GGG AAG AAG AAT GAT GAA GTG TCC AGC CTG GAT GCC         534
Gln Leu Gly Pro Gly Lys Lys Asn Asp Glu Val Ser Ser Leu Asp Ala
    695             700             705

TTC CTG GAC CTT ATT CGA AAT CTC TTC CCT GAA AAC CTT GTC CAA GCC         582
Phe Leu Asp Leu Ile Arg Asn Leu Phe Pro Glu Asn Leu Val Gln Ala
710             715             720             725

TGC TTT CAA CAG ATT CAA ACA GTG ACG AAG AAA GTC CTG GTT GCA CCA         630
Cys Phe Gln Gln Ile Gln Thr Val Thr Lys Lys Val Leu Val Ala Pro
            730             735             740

CCG CCA GAC GAG GAG GCC AAC GCA ACC AGC GCT GAA GTC TCT CTG TTG         678
Pro Pro Asp Glu Glu Ala Asn Ala Thr Ser Ala Glu Val Ser Leu Leu
            745             750             755

AAC GAG ACT GTG ACT GAG GTG CCG GAG GAG ACT AAG ATG GTT ATC AAG         726
```

```
       Asn Glu Thr Val Thr Glu Val Pro Glu Glu Thr Lys Met Val Ile Lys
           760                 765                 770

AAG GGC CTG GAG TTC AAG GAT GGG ATG AAC GTC TTA GGT CTG ATA GGG              774
Lys Gly Leu Glu Phe Lys Asp Gly Met Asn Val Leu Gly Leu Ile Gly
    775                 780                 785

TTT TTC ATT GCT TTT GGC ATC GCT ATG GGG AAG ATG GGA GAT CAG GCC              822
Phe Phe Ile Ala Phe Gly Ile Ala Met Gly Lys Met Gly Asp Gln Ala
790                 795                 800                 805

AAG CTG ATG GTG GAT TTC TTC AAC ATT TTG AAT GAG ATT GTA ATG AAG              870
Lys Leu Met Val Asp Phe Phe Asn Ile Leu Asn Glu Ile Val Met Lys
                810                 815                 820

TTA GTG ATC ATG ATC ATG TGG TAC TCT CCC CTG GGT ATC GCC TGC CTG              918
Leu Val Ile Met Ile Met Trp Tyr Ser Pro Leu Gly Ile Ala Cys Leu
            825                 830                 835

ATC TGT GGA AAG ATC ATT GCA ATC AAG GAC TTA GAA GTG GTT GCT AGG              966
Ile Cys Gly Lys Ile Ile Ala Ile Lys Asp Leu Glu Val Val Ala Arg
        840                 845                 850

CAA CTG GGG ATG TAC ATG GTA ACA GTG ATC ATA GGC CTC ATC ATC CAC             1014
Gln Leu Gly Met Tyr Met Val Thr Val Ile Ile Gly Leu Ile Ile His
    855                 860                 865

GGG GGC ATC TTT CTC CCC TTG ATT TAC TTT GTA GTG ACC AGG AAA AAC             1062
Gly Gly Ile Phe Leu Pro Leu Ile Tyr Phe Val Val Thr Arg Lys Asn
870                 875                 880                 885

CCC TTC TCC CTT TTT GCT GGC ATT TTC CAA GCT TGG ATC ACT GCC CTG             1110
Pro Phe Ser Leu Phe Ala Gly Ile Phe Gln Ala Trp Ile Thr Ala Leu
                890                 895                 900

GGC ACC GCT TCC AGT GCT GGA ACT TTG CCT GTC ACC TTT CGT TGC CTG             1158
Gly Thr Ala Ser Ser Ala Gly Thr Leu Pro Val Thr Phe Arg Cys Leu
            905                 910                 915

GAA GAA AAT CTG GGG ATT GAT AAG CGT GTG ACT AGA TTC GTC CTT CCT             1206
Glu Glu Asn Leu Gly Ile Asp Lys Arg Val Thr Arg Phe Val Leu Pro
        920                 925                 930

GTT GGA GCA ACC ATT AAC ATG GAT GGT ACA GCC CTT TAT GAA GCG GTG             1254
Val Gly Ala Thr Ile Asn Met Asp Gly Thr Ala Leu Tyr Glu Ala Val
    935                 940                 945

GCC GCC ATC TTT ATA GCC CAA ATG AAT GGT GTT GTC CTG GAT GGA GGA             1302
Ala Ala Ile Phe Ile Ala Gln Met Asn Gly Val Val Leu Asp Gly Gly
950                 955                 960                 965

CAG ATT GTG ACT GTA AGC CTC ACA GCC ACC CTG GCA AGC GTC GGC GCG             1350
Gln Ile Val Thr Val Ser Leu Thr Ala Thr Leu Ala Ser Val Gly Ala
                970                 975                 980

GCC AGT ATC CCC AGT GCC GGG CTG GTC ACC ATG CTC CTC ATT CTG ACA             1398
Ala Ser Ile Pro Ser Ala Gly Leu Val Thr Met Leu Leu Ile Leu Thr
            985                 990                 995

GCC GTG GGC CTG CCA ACA GAG GAC ATC AGC TTG CTG GTG GCT GTG GAC             1446
Ala Val Gly Leu Pro Thr Glu Asp Ile Ser Leu Leu Val Ala Val Asp
        1000                1005                1010

TGG CTG CTG GAC AGG ATG AGA ACT TCA GTC AAT GTT GTG GGT GAC TCT             1494
Trp Leu Leu Asp Arg Met Arg Thr Ser Val Asn Val Val Gly Asp Ser
    1015                1020                1025

TTT GGG GCT GGG ATA GTC TAT CAC CTC TCC AAG TCT GAG CTG GAT ACC             1542
Phe Gly Ala Gly Ile Val Tyr His Leu Ser Lys Ser Glu Leu Asp Thr
1030                1035                1040                1045

ATT GAC TCC CAG CAT CGA GTG CAT GAA GAT ATT GAA ATG ACC AAG ACT             1590
Ile Asp Ser Gln His Arg Val His Glu Asp Ile Glu Met Thr Lys Thr
                1050                1055                1060

CAA TCC ATT TAT GAT GAC ATG AAG AAC CAC AGG GAA AGC AAC TCT AAT             1638
Gln Ser Ile Tyr Asp Asp Met Lys Asn His Arg Glu Ser Asn Ser Asn
            1065                1070                1075

CAA TGT GTC TAT GCT GCA CAC AAC TCT GTC ATA GTA GAT GAA TGC AAG             1686
```

| | | | | | | | | | | | | | | |
|---|---|---|---|---|---|---|---|---|---|---|---|---|---|---|
|Gln|Cys|Val|Tyr|Ala|Ala|His|Asn|Ser|Val|Ile|Val|Asp|Glu|Cys|Lys|
| | |1080| | | |1085| | | |1090| | | | |

GTA ACT CTG GCA GCC AAT GGA AAG TCA GCC GAC TGC AGT GTT GAG GAA   1734
Val Thr Leu Ala Ala Asn Gly Lys Ser Ala Asp Cys Ser Val Glu Glu
    1095            1100            1105

GAA CCT TGG AAA CGT GAG AAA TAAGGATATG AGTCTCAGCA AATTCTTGAA   1785
Glu Pro Trp Lys Arg Glu Lys
1110            1115

TAAACTCCCC AGCGT   1800

( 2 ) INFORMATION FOR SEQ ID NO:4:

( i ) SEQUENCE CHARACTERISTICS:
        ( A ) LENGTH: 574 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Met Ala Ser Thr Glu Gly Ala Asn Asn Met Pro Lys Gln Val Glu Val
 1               5                  10                  15

Arg Met Pro Asp Ser His Leu Gly Ser Glu Glu Pro Lys His Arg His
              20                  25                  30

Leu Gly Leu Arg Leu Cys Asp Lys Leu Gly Lys Asn Leu Leu Thr
          35                  40                  45

Leu Thr Val Phe Gly Val Thr Leu Gly Ala Val Cys Gly Leu Leu
     50                  55                  60

Arg Leu Ala Ser Pro Ile His Pro Asp Val Val Met Leu Ile Ala Phe
 65                  70                  75                  80

Pro Gly Asp Ile Leu Met Arg Met Leu Lys Met Leu Ile Leu Gly Leu
                 85                  90                  95

Ile Ile Ser Ser Leu Ile Thr Gly Leu Ser Gly Leu Asp Ala Lys Ala
             100                 105                 110

Ser Gly Arg Leu Gly Thr Arg Ala Met Val Tyr Tyr Met Ser Thr Thr
             115                 120                 125

Ile Ile Ala Ala Val Leu Gly Val Ile Leu Val Leu Ala Ile His Pro
    130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
                180                 185                 190

Lys Lys Val Leu Val Ala Pro Pro Asp Glu Glu Ala Asn Ala Thr
         195                 200                 205

Ser Ala Glu Val Ser Leu Leu Asn Glu Thr Val Thr Glu Val Pro Glu
    210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255

Gly Lys Met Gly Asp Gln Ala Lys Leu Met Val Asp Phe Phe Asn Ile
             260                 265                 270

Leu Asn Glu Ile Val Met Lys Leu Val Ile Met Ile Met Trp Tyr Ser
         275                 280                 285

Pro Leu Gly Ile Ala Cys Leu Ile Cys Gly Lys Ile Ile Ala Ile Lys

|     |     |     |     |     |     | 290 |     |     |     |     |     | 295 |     |     |     |     |     | 300 |     |     |
|---|---|---|---|---|---|---|---|---|---|---|---|---|---|---|---|---|---|---|---|---|

Asp Leu Glu Val Val Ala Arg Gln Leu Gly Met Tyr Met Val Thr Val
305                     310                 315                 320

Ile Ile Gly Leu Ile Ile His Gly Gly Ile Phe Leu Pro Leu Ile Tyr
                325                 330                 335

Phe Val Val Thr Arg Lys Asn Pro Phe Ser Leu Phe Ala Gly Ile Phe
            340                 345                 350

Gln Ala Trp Ile Thr Ala Leu Gly Thr Ala Ser Ser Ala Gly Thr Leu
        355                 360                 365

Pro Val Thr Phe Arg Cys Leu Glu Glu Asn Leu Gly Ile Asp Lys Arg
    370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
                405                 410                 415

Gly Val Val Leu Asp Gly Gly Gln Ile Val Thr Val Ser Leu Thr Ala
            420                 425                 430

Thr Leu Ala Ser Val Gly Ala Ala Ser Ile Pro Ser Ala Gly Leu Val
        435                 440                 445

Thr Met Leu Leu Ile Leu Thr Ala Val Gly Leu Pro Thr Glu Asp Ile
    450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
                485                 490                 495

Ser Lys Ser Glu Leu Asp Thr Ile Asp Ser Gln His Arg Val His Glu
            500                 505                 510

Asp Ile Glu Met Thr Lys Thr Gln Ser Ile Tyr Asp Asp Met Lys Asn
        515                 520                 525

His Arg Glu Ser Asn Ser Asn Gln Cys Val Tyr Ala Ala His Asn Ser
    530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
                565                 570

( 2 ) INFORMATION FOR SEQ ID NO:5:

( i ) SEQUENCE CHARACTERISTICS:
        ( A ) LENGTH: 1674 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 16..1590

( x i ) SEQUENCE DESCRIPTION: SEQ ID NO:5:

ATAGCGGCGA CAGCC ATG GGG AAA CCG GCG AGG AAA GGA TGC CCG AGT TGG          51
               Met Gly Lys Pro Ala Arg Lys Gly Cys Pro Ser Trp
               575                 580                 585

AAG CGC TTC CTG AAG AAT AAC TGG GTG TTG CTG TCC ACC GTG GCC GCG          99
Lys Arg Phe Leu Lys Asn Asn Trp Val Leu Leu Ser Thr Val Ala Ala
                590                 595                 600

GTG GTG CTA GGC ATT ACC ACA GGA GTC TTG GTT CGA GAA CAC AGC AAC          147
Val Val Leu Gly Ile Thr Thr Gly Val Leu Val Arg Glu His Ser Asn

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |  605 |    |     |     |     | 610 |     |     |     |     |     | 615 |     |     |
| CTC | TCA | ACT | CTA | GAG | AAA | TTC | TAC | TTT | GCT | TTT | CCT | GGA | GAA | ATT | CTA | 195 |
| Leu | Ser | Thr | Leu | Glu | Lys | Phe | Tyr | Phe | Ala | Phe | Pro | Gly | Glu | Ile | Leu |
|     | 620 |     |     |     | 625 |     |     |     |     | 630 |     |     |     |     |     |
| ATG | CGG | ATG | CTG | AAA | CTC | ATC | ATT | TTG | CCA | TTA | ATT | ATA | TCC | AGC | ATG | 243 |
| Met | Arg | Met | Leu | Lys | Leu | Ile | Ile | Leu | Pro | Leu | Ile | Ile | Ser | Ser | Met |
| 635 |     |     |     |     | 640 |     |     |     |     | 645 |     |     |     |     | 650 |
| ATT | ACA | GGT | GTT | GCT | GCA | CTG | GAT | TCC | AAC | GTA | TCC | GGA | AAA | ATT | GGT | 291 |
| Ile | Thr | Gly | Val | Ala | Ala | Leu | Asp | Ser | Asn | Val | Ser | Gly | Lys | Ile | Gly |
|     |     |     |     | 655 |     |     |     |     | 660 |     |     |     |     | 665 |     |
| CTG | CGC | GCT | GTC | GTG | TAT | TAT | TTC | TGT | ACC | ACT | CTC | ATT | GCT | GTT | ATT | 339 |
| Leu | Arg | Ala | Val | Val | Tyr | Tyr | Phe | Cys | Thr | Thr | Leu | Ile | Ala | Val | Ile |
|     |     |     | 670 |     |     |     |     | 675 |     |     |     |     | 680 |     |     |
| CTA | GGT | ATT | GTG | CTG | GTG | GTG | AGC | ATC | AAG | CCT | GGT | GTC | ACC | CAG | AAA | 387 |
| Leu | Gly | Ile | Val | Leu | Val | Val | Ser | Ile | Lys | Pro | Gly | Val | Thr | Gln | Lys |
|     |     | 685 |     |     |     |     | 690 |     |     |     |     | 695 |     |     |     |
| GTG | GGT | GAA | ATT | GCG | AGG | ACA | GGC | AGC | ACC | CCT | GAA | GTC | AGT | ACG | GTG | 435 |
| Val | Gly | Glu | Ile | Ala | Arg | Thr | Gly | Ser | Thr | Pro | Glu | Val | Ser | Thr | Val |
|     |     | 700 |     |     |     |     | 705 |     |     |     |     | 710 |     |     |     |
| GAT | GCC | ATG | TTA | GAT | CTC | ATC | AGG | AAT | ATG | TTC | CCT | GAG | AAT | CTT | GTC | 483 |
| Asp | Ala | Met | Leu | Asp | Leu | Ile | Arg | Asn | Met | Phe | Pro | Glu | Asn | Leu | Val |
| 715 |     |     |     |     | 720 |     |     |     |     | 725 |     |     |     |     | 730 |
| CAG | GCC | TGT | TTT | CAG | CAG | TAC | AAA | ACT | AAG | CGT | GAA | GAA | GTG | AAG | CCT | 531 |
| Gln | Ala | Cys | Phe | Gln | Gln | Tyr | Lys | Thr | Lys | Arg | Glu | Glu | Val | Lys | Pro |
|     |     |     |     | 735 |     |     |     |     | 740 |     |     |     |     | 745 |     |
| CCC | AGC | GAT | CCA | GAG | ATG | AAC | ATG | ACA | GAA | GAG | TCC | TTC | ACA | GCT | GTC | 579 |
| Pro | Ser | Asp | Pro | Glu | Met | Asn | Met | Thr | Glu | Glu | Ser | Phe | Thr | Ala | Val |
|     |     |     | 750 |     |     |     |     | 755 |     |     |     |     | 760 |     |     |
| ATG | ACA | ACT | GCA | ATT | TCC | AAG | AAC | AAA | ACA | AAG | GAA | TAC | AAA | ATT | GTT | 627 |
| Met | Thr | Thr | Ala | Ile | Ser | Lys | Asn | Lys | Thr | Lys | Glu | Tyr | Lys | Ile | Val |
|     |     | 765 |     |     |     |     | 770 |     |     |     |     | 775 |     |     |     |
| GGC | ATG | TAT | TCA | GAT | GGC | ATA | AAC | GTC | CTG | GGC | TTG | ATT | GTC | TTT | TGC | 675 |
| Gly | Met | Tyr | Ser | Asp | Gly | Ile | Asn | Val | Leu | Gly | Leu | Ile | Val | Phe | Cys |
|     | 780 |     |     |     |     | 785 |     |     |     |     | 790 |     |     |     |     |
| CTT | GTC | TTT | GGA | CTT | GTC | ATT | GGA | AAA | ATG | GGA | GAA | AAG | GGA | CAA | ATT | 723 |
| Leu | Val | Phe | Gly | Leu | Val | Ile | Gly | Lys | Met | Gly | Glu | Lys | Gly | Gln | Ile |
| 795 |     |     |     |     | 800 |     |     |     |     | 805 |     |     |     |     | 810 |
| CTG | GTG | GAT | TTC | TTC | AAT | GCT | TTG | AGT | GAT | GCA | ACC | ATG | AAA | ATC | GTT | 771 |
| Leu | Val | Asp | Phe | Phe | Asn | Ala | Leu | Ser | Asp | Ala | Thr | Met | Lys | Ile | Val |
|     |     |     |     | 815 |     |     |     |     | 820 |     |     |     |     | 825 |     |
| CAG | ATC | ATC | ATG | TGT | TAT | ATG | CCA | CTA | GGT | ATT | TTG | TTC | CTG | ATT | GCT | 819 |
| Gln | Ile | Ile | Met | Cys | Tyr | Met | Pro | Leu | Gly | Ile | Leu | Phe | Leu | Ile | Ala |
|     |     |     | 830 |     |     |     |     | 835 |     |     |     |     | 840 |     |     |
| GGG | AAG | ATC | ATA | GAA | GTT | GAA | GAC | TGG | GAA | ATA | TTC | CGC | AAG | CTG | GGC | 867 |
| Gly | Lys | Ile | Ile | Glu | Val | Glu | Asp | Trp | Glu | Ile | Phe | Arg | Lys | Leu | Gly |
|     |     | 845 |     |     |     |     | 850 |     |     |     |     | 855 |     |     |     |
| CTT | TAC | ATG | GCC | ACA | GTC | CTG | ACT | GGG | CTT | GCA | ATC | CAC | TCC | ATT | GTA | 915 |
| Leu | Tyr | Met | Ala | Thr | Val | Leu | Thr | Gly | Leu | Ala | Ile | His | Ser | Ile | Val |
|     | 860 |     |     |     |     | 865 |     |     |     |     | 870 |     |     |     |     |
| ATT | CTC | CCG | CTG | ATA | TAT | TTC | ATA | GTC | GTA | CGA | AAG | AAC | CCT | TTC | CGA | 963 |
| Ile | Leu | Pro | Leu | Ile | Tyr | Phe | Ile | Val | Val | Arg | Lys | Asn | Pro | Phe | Arg |
| 875 |     |     |     |     | 880 |     |     |     |     | 885 |     |     |     |     | 890 |
| TTT | GCC | ATG | GGA | ATG | GCC | CAG | GCT | CTC | CTG | ACA | GCT | CTC | ATG | ATC | TCT | 1011 |
| Phe | Ala | Met | Gly | Met | Ala | Gln | Ala | Leu | Leu | Thr | Ala | Leu | Met | Ile | Ser |
|     |     |     |     | 895 |     |     |     |     | 900 |     |     |     |     | 905 |     |
| TCC | AGT | TCA | GCA | ACA | CTG | CCT | GTC | ACC | TTC | CGC | TGT | GCT | GAA | GAA | AAT | 1059 |
| Ser | Ser | Ser | Ala | Thr | Leu | Pro | Val | Thr | Phe | Arg | Cys | Ala | Glu | Glu | Asn |
|     |     |     | 910 |     |     |     |     | 915 |     |     |     |     | 920 |     |     |
| AAC | CAG | GTG | GAC | AAG | AGG | ATC | ACT | CGA | TTC | GTG | TTA | CCC | GTT | GGT | GCA | 1107 |
| Asn | Gln | Val | Asp | Lys | Arg | Ile | Thr | Arg | Phe | Val | Leu | Pro | Val | Gly | Ala |

-continued

```
                       925                         930                         935
ACA  ATC  AAC  ATG  GAT  GGG  ACC  GCG  CTC  TAT  GAA  GCA  GTG  GCA  GCG  GTG           1155
Thr  Ile  Asn  Met  Asp  Gly  Thr  Ala  Leu  Tyr  Glu  Ala  Val  Ala  Ala  Val
     940                           945                      950

TTT  ATT  GCA  CAG  TTG  AAT  GAC  CTG  GAC  TTG  GGC  ATT  GGG  CAG  ATC  ATC           1203
Phe  Ile  Ala  Gln  Leu  Asn  Asp  Leu  Asp  Leu  Gly  Ile  Gly  Gln  Ile  Ile
955                           960                      965                      970

ACC  ATC  AGT  ATC  ACG  GCC  ACA  TCT  GCC  AGC  ATC  GGA  GCT  GCT  GGC  GTG           1251
Thr  Ile  Ser  Ile  Thr  Ala  Thr  Ser  Ala  Ser  Ile  Gly  Ala  Ala  Gly  Val
               975                      980                           985

CCC  CAG  GCT  GGC  CTG  GTG  ACC  ATG  GTG  ATT  GTG  CTG  AGT  GCC  GTG  GGC           1299
Pro  Gln  Ala  Gly  Leu  Val  Thr  Met  Val  Ile  Val  Leu  Ser  Ala  Val  Gly
               990                      995                      1000

CTG  CCC  GCC  GAG  GAT  GTC  ACC  CTG  ATC  ATT  GCT  GTC  GAC  TGG  CTC  TCG           1347
Leu  Pro  Ala  Glu  Asp  Val  Thr  Leu  Ile  Ile  Ala  Val  Asp  Trp  Leu  Ser
               1005                     1010                     1015

GAC  CGG  TTC  AGG  ACC  ATG  GTC  AAC  GTC  CTT  GGT  GAT  GCT  TTT  GGG  ACG           1395
Asp  Arg  Phe  Arg  Thr  Met  Val  Asn  Val  Leu  Gly  Asp  Ala  Phe  Gly  Thr
     1020                          1025                     1030

GGC  ATT  GTG  GAA  AAG  CTC  TCC  AAG  AAG  GAG  CTG  GAG  CAG  ATG  GAT  GTT           1443
Gly  Ile  Val  Glu  Lys  Leu  Ser  Lys  Lys  Glu  Leu  Glu  Gln  Met  Asp  Val
1035                     1040                     1045                     1050

TCA  TCT  GAA  GTC  AAC  ATT  GTG  AAT  CCC  TTT  GCC  TTG  GAA  TCC  ACA  ATC           1491
Ser  Ser  Glu  Val  Asn  Ile  Val  Asn  Pro  Phe  Ala  Leu  Glu  Ser  Thr  Ile
                         1055                     1060                     1065

CTT  GAC  AAC  GAA  GAC  TCA  GAC  ACC  AAG  AAG  TCT  TAT  GTC  AAT  GGA  GGC           1539
Leu  Asp  Asn  Glu  Asp  Ser  Asp  Thr  Lys  Lys  Ser  Tyr  Val  Asn  Gly  Gly
                    1070                     1075                     1080

TTT  GCA  GTA  GAC  AAG  TCT  GAC  ACC  ATC  TCA  TTC  ACC  CAG  ACC  TCA  CAG           1587
Phe  Ala  Val  Asp  Lys  Ser  Asp  Thr  Ile  Ser  Phe  Thr  Gln  Thr  Ser  Gln
               1085                     1090                     1095

TTC  TAGGGCCCCT  GGCTGCAGAT  GACTGGAAAC  AAGGAAGGAC  ATTTCGTGAG                          1640
Phe

AGTCATCTCA  AACACGGCTT  AAGGAAAAGA  GAAA                                                 1674
```

( 2 ) INFORMATION FOR SEQ ID NO:6:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Gly  Lys  Pro  Ala  Arg  Lys  Gly  Cys  Pro  Ser  Trp  Lys  Arg  Phe  Leu
1                   5                        10                       15

Lys  Asn  Asn  Trp  Val  Leu  Leu  Ser  Thr  Val  Ala  Ala  Val  Val  Leu  Gly
               20                       25                       30

Ile  Thr  Thr  Gly  Val  Leu  Val  Arg  Glu  His  Ser  Asn  Leu  Ser  Thr  Leu
          35                       40                       45

Glu  Lys  Phe  Tyr  Phe  Ala  Phe  Pro  Gly  Glu  Ile  Leu  Met  Arg  Met  Leu
     50                       55                       60

Lys  Leu  Ile  Ile  Leu  Pro  Leu  Ile  Ile  Ser  Ser  Met  Ile  Thr  Gly  Val
65                       70                       75                       80

Ala  Ala  Leu  Asp  Ser  Asn  Val  Ser  Gly  Lys  Ile  Gly  Leu  Arg  Ala  Val
                    85                       90                       95

Val  Tyr  Tyr  Phe  Cys  Thr  Thr  Leu  Ile  Ala  Val  Ile  Leu  Gly  Ile  Val
               100                      105                      110
```

| Leu | Val | Val | Ser | Ile | Lys | Pro | Val | Thr | Gln | Lys | Val | Gly | Glu | Ile |
|---|---|---|---|---|---|---|---|---|---|---|---|---|---|---|
| | | 115 | | | | 120 | | | | 125 | | | | |

| Ala | Arg | Thr | Gly | Ser | Thr | Pro | Glu | Val | Ser | Thr | Val | Asp | Ala | Met | Leu |
|---|---|---|---|---|---|---|---|---|---|---|---|---|---|---|---|
| | 130 | | | | | 135 | | | | 140 | | | | | |

| Asp | Leu | Ile | Arg | Asn | Met | Phe | Pro | Glu | Asn | Leu | Val | Gln | Ala | Cys | Phe |
|---|---|---|---|---|---|---|---|---|---|---|---|---|---|---|---|
| 145 | | | | | 150 | | | | | 155 | | | | | 160 |

| Gln | Gln | Tyr | Lys | Thr | Lys | Arg | Glu | Glu | Val | Lys | Pro | Pro | Ser | Asp | Pro |
|---|---|---|---|---|---|---|---|---|---|---|---|---|---|---|---|
| | | | | 165 | | | | | 170 | | | | | 175 | |

| Glu | Met | Asn | Met | Thr | Glu | Glu | Ser | Phe | Thr | Ala | Val | Met | Thr | Thr | Ala |
|---|---|---|---|---|---|---|---|---|---|---|---|---|---|---|---|
| | | | 180 | | | | | 185 | | | | | 190 | | |

| Ile | Ser | Lys | Asn | Lys | Thr | Lys | Glu | Tyr | Lys | Ile | Val | Gly | Met | Tyr | Ser |
|---|---|---|---|---|---|---|---|---|---|---|---|---|---|---|---|
| | | 195 | | | | | 200 | | | | | 205 | | | |

| Asp | Gly | Ile | Asn | Val | Leu | Gly | Leu | Ile | Val | Phe | Cys | Leu | Val | Phe | Gly |
|---|---|---|---|---|---|---|---|---|---|---|---|---|---|---|---|
| | 210 | | | | | 215 | | | | | 220 | | | | |

| Leu | Val | Ile | Gly | Lys | Met | Gly | Glu | Lys | Gly | Gln | Ile | Leu | Val | Asp | Phe |
|---|---|---|---|---|---|---|---|---|---|---|---|---|---|---|---|
| 225 | | | | | 230 | | | | | 235 | | | | | 240 |

| Phe | Asn | Ala | Leu | Ser | Asp | Ala | Thr | Met | Lys | Ile | Val | Gln | Ile | Ile | Met |
|---|---|---|---|---|---|---|---|---|---|---|---|---|---|---|---|
| | | | | 245 | | | | | 250 | | | | | 255 | |

| Cys | Tyr | Met | Pro | Leu | Gly | Ile | Leu | Phe | Leu | Ile | Ala | Gly | Lys | Ile | Ile |
|---|---|---|---|---|---|---|---|---|---|---|---|---|---|---|---|
| | | | 260 | | | | | 265 | | | | | 270 | | |

| Glu | Val | Glu | Asp | Trp | Glu | Ile | Phe | Arg | Lys | Leu | Gly | Leu | Tyr | Met | Ala |
|---|---|---|---|---|---|---|---|---|---|---|---|---|---|---|---|
| | | 275 | | | | | 280 | | | | | 285 | | | |

| Thr | Val | Leu | Thr | Gly | Leu | Ala | Ile | His | Ser | Ile | Val | Ile | Leu | Pro | Leu |
|---|---|---|---|---|---|---|---|---|---|---|---|---|---|---|---|
| | 290 | | | | | 295 | | | | | 300 | | | | |

| Ile | Tyr | Phe | Ile | Val | Val | Arg | Lys | Asn | Pro | Phe | Arg | Phe | Ala | Met | Gly |
|---|---|---|---|---|---|---|---|---|---|---|---|---|---|---|---|
| 305 | | | | | 310 | | | | | 315 | | | | | 320 |

| Met | Ala | Gln | Ala | Leu | Leu | Thr | Ala | Leu | Met | Ile | Ser | Ser | Ser | Ser | Ala |
|---|---|---|---|---|---|---|---|---|---|---|---|---|---|---|---|
| | | | | 325 | | | | | 330 | | | | | 335 | |

| Thr | Leu | Pro | Val | Thr | Phe | Arg | Cys | Ala | Glu | Glu | Asn | Asn | Gln | Val | Asp |
|---|---|---|---|---|---|---|---|---|---|---|---|---|---|---|---|
| | | | 340 | | | | | 345 | | | | | 350 | | |

| Lys | Arg | Ile | Thr | Arg | Phe | Val | Leu | Pro | Val | Gly | Ala | Thr | Ile | Asn | Met |
|---|---|---|---|---|---|---|---|---|---|---|---|---|---|---|---|
| | | 355 | | | | | 360 | | | | | 365 | | | |

| Asp | Gly | Thr | Ala | Leu | Tyr | Glu | Ala | Val | Ala | Ala | Val | Phe | Ile | Ala | Gln |
|---|---|---|---|---|---|---|---|---|---|---|---|---|---|---|---|
| | 370 | | | | | 375 | | | | | 380 | | | | |

| Leu | Asn | Asp | Leu | Asp | Leu | Gly | Ile | Gly | Gln | Ile | Ile | Thr | Ile | Ser | Ile |
|---|---|---|---|---|---|---|---|---|---|---|---|---|---|---|---|
| 385 | | | | | 390 | | | | | 395 | | | | | 400 |

| Thr | Ala | Thr | Ser | Ala | Ser | Ile | Gly | Ala | Ala | Gly | Val | Pro | Gln | Ala | Gly |
|---|---|---|---|---|---|---|---|---|---|---|---|---|---|---|---|
| | | | | 405 | | | | | 410 | | | | | 415 | |

| Leu | Val | Thr | Met | Val | Ile | Val | Leu | Ser | Ala | Val | Gly | Leu | Pro | Ala | Glu |
|---|---|---|---|---|---|---|---|---|---|---|---|---|---|---|---|
| | | | 420 | | | | | 425 | | | | | 430 | | |

| Asp | Val | Thr | Leu | Ile | Ile | Ala | Val | Asp | Trp | Leu | Ser | Asp | Arg | Phe | Arg |
|---|---|---|---|---|---|---|---|---|---|---|---|---|---|---|---|
| | | 435 | | | | | 440 | | | | | 445 | | | |

| Thr | Met | Val | Asn | Val | Leu | Gly | Asp | Ala | Phe | Gly | Thr | Gly | Ile | Val | Glu |
|---|---|---|---|---|---|---|---|---|---|---|---|---|---|---|---|
| | 450 | | | | | 455 | | | | | 460 | | | | |

| Lys | Leu | Ser | Lys | Lys | Glu | Leu | Glu | Gln | Met | Asp | Val | Ser | Ser | Glu | Val |
|---|---|---|---|---|---|---|---|---|---|---|---|---|---|---|---|
| 465 | | | | | 470 | | | | | 475 | | | | | 480 |

| Asn | Ile | Val | Asn | Pro | Phe | Ala | Leu | Glu | Ser | Thr | Ile | Leu | Asp | Asn | Glu |
|---|---|---|---|---|---|---|---|---|---|---|---|---|---|---|---|
| | | | | 485 | | | | | 490 | | | | | 495 | |

| Asp | Ser | Asp | Thr | Lys | Lys | Ser | Tyr | Val | Asn | Gly | Gly | Phe | Ala | Val | Asp |
|---|---|---|---|---|---|---|---|---|---|---|---|---|---|---|---|
| | | | 500 | | | | | 505 | | | | | 510 | | |

| Lys | Ser | Asp | Thr | Ile | Ser | Phe | Thr | Gln | Thr | Ser | Gln | Phe |
|---|---|---|---|---|---|---|---|---|---|---|---|---|
| | | | 515 | | | | | 520 | | | | 525 |

( 2 ) INFORMATION FOR SEQ ID NO:7:

(i) SEQUENCE CHARACTERISTICS:
   (A) LENGTH: 1734 base pairs
   (B) TYPE: nucleic acid
   (C) STRANDEDNESS: single
   (D) TOPOLOGY: linear (ii) MOLECULE TYPE: cDNA (ix) FEATURE:
   (A) NAME/KEY: CDS
   (B) LOCATION: 9..1700

(xi) SEQUENCE DESCRIPTION: SEQ ID NO:7:

```
GATAGACC ATG AGC AGC CAT GGC AAC AGC CTG TTC CTT CGG GAG AGC GGC         50
         Met Ser Ser His Gly Asn Ser Leu Phe Leu Arg Glu Ser Gly
         1               5                   10

CAG CGG CTG GGC CGG GTG GGC TGG CTG CAG CGG CTG CAG GAA AGC CTG          98
Gln Arg Leu Gly Arg Val Gly Trp Leu Gln Arg Leu Gln Glu Ser Leu
15              20                  25                  30

CAG CAG AGA GCA CTG CGC ACG CGC CTG CGC CTG CAG ACC ATG ACC CTC         146
Gln Gln Arg Ala Leu Arg Thr Arg Leu Arg Leu Gln Thr Met Thr Leu
                35                  40                  45

GAG CAC GTG CTG CGC TTC CTG CGC CGA AAC GCC TTC ATT CTG CTG ACG         194
Glu His Val Leu Arg Phe Leu Arg Arg Asn Ala Phe Ile Leu Leu Thr
                50                  55                  60

GTC AGC GCC GTG GTC ATT GGG GTC AGC CTG GCC TTT GCC CTG CGC CCA         242
Val Ser Ala Val Val Ile Gly Val Ser Leu Ala Phe Ala Leu Arg Pro
            65                  70                  75

TAT CAG CTC ACC TAC CGC CAG ATC AAG TAC TTC TCT TTT CCT GGA GAG         290
Tyr Gln Leu Thr Tyr Arg Gln Ile Lys Tyr Phe Ser Phe Pro Gly Glu
        80                  85                  90

CTT CTG ATG AGG ATG CTG CAG ATG CTG GTG TTA CCT CTC ATT GTC TCC         338
Leu Leu Met Arg Met Leu Gln Met Leu Val Leu Pro Leu Ile Val Ser
95                  100                 105                 110

AGC CTG GTC ACA GGT ATG GCA TCC CTG GAC AAC AAG GCC ACG GGG CGG         386
Ser Leu Val Thr Gly Met Ala Ser Leu Asp Asn Lys Ala Thr Gly Arg
                115                 120                 125

ATG GGG ATG CGG GCA GCT GTG TAC TAC CTG GTG ACC ACC ATC ATC GCG         434
Met Gly Met Arg Ala Ala Val Tyr Tyr Leu Val Thr Thr Ile Ile Ala
                130                 135                 140

GTC TTC ATC GGC ATC CTC ATG GTC ACC ATC ATC CAT CCC GGG AAG GGC         482
Val Phe Ile Gly Ile Leu Met Val Thr Ile Ile His Pro Gly Lys Gly
            145                 150                 155

TCC AAG GAG GGG CTG CAC CGG GAG GGC CGG ATC GAG ACC ATC CCC ACA         530
Ser Lys Glu Gly Leu His Arg Glu Gly Arg Ile Glu Thr Ile Pro Thr
        160                 165                 170

GCT GAT GCC TTC ATG GAC CTG ATC AGA AAT ATG TTT CCA CCA AAC CTT         578
Ala Asp Ala Phe Met Asp Leu Ile Arg Asn Met Phe Pro Pro Asn Leu
175                 180                 185                 190

GTG GAG GCC TGC TTC AAA CAG TTG AAG ACG CAG TAC AGC ACG AGG GTG         626
Val Glu Ala Cys Phe Lys Gln Leu Lys Thr Gln Tyr Ser Thr Arg Val
                195                 200                 205

GTA ACC AGG ACC ATG GTG AGG ACA GAG AAC GGG TCT GAG CCG GGT GCC         674
Val Thr Arg Thr Met Val Arg Thr Glu Asn Gly Ser Glu Pro Gly Ala
                210                 215                 220

TCC ATG CCT CCT CCA TTC TCA GTG GAG AAC GGA ACC AGC TTC CTG GAA         722
Ser Met Pro Pro Pro Phe Ser Val Glu Asn Gly Thr Ser Phe Leu Glu
            225                 230                 235

AAT GTC ACT CGG GCC TTG GGT ACC CTG CAG GAG ATG CTG AGC TTT GAG         770
Asn Val Thr Arg Ala Leu Gly Thr Leu Gln Glu Met Leu Ser Phe Glu
        240                 245                 250

GAG ACT GTA CCC GTG CCT GGC TCC GCC AAT GGC ATC AAC GCC CTG GGC         818
Glu Thr Val Pro Val Pro Gly Ser Ala Asn Gly Ile Asn Ala Leu Gly
```

| | | | | | | | | | | | | | | | | |
|---|---|---|---|---|---|---|---|---|---|---|---|---|---|---|---|---|
| | Glu | Thr | Val | Pro | Val | Pro | Gly | Ser | Ala | Asn | Gly | Ile | Asn | Ala | Leu | Gly |
| | 255 | | | | 260 | | | | | 265 | | | | | 270 | |
| CTC | GTG | GTC | TTC | TCT | GTG | GCC | TTT | GGG | CTG | GTC | ATT | GGT | GGC | ATG | AAA | 866 |
| Leu | Val | Val | Phe | Ser | Val | Ala | Phe | Gly | Leu | Val | Ile | Gly | Gly | Met | Lys | |
| | | | | 275 | | | | | 280 | | | | | 285 | | |
| CAC | AAG | GGC | AGA | GTC | CTC | AGG | GAC | TTC | TTC | GAC | AGC | CTC | AAT | GAG | GCT | 914 |
| His | Lys | Gly | Arg | Val | Leu | Arg | Asp | Phe | Phe | Asp | Ser | Leu | Asn | Glu | Ala | |
| | | | 290 | | | | | 295 | | | | | 300 | | | |
| ATT | ATG | AGG | CTG | GTG | GGC | ATC | ATT | ATC | TGG | TAT | GCA | CCT | GTG | GGC | ATC | 962 |
| Ile | Met | Arg | Leu | Val | Gly | Ile | Ile | Ile | Trp | Tyr | Ala | Pro | Val | Gly | Ile | |
| | | 305 | | | | | 310 | | | | | 315 | | | | |
| CTG | TTC | CTG | ATT | GCT | GGG | AAG | ATT | CTG | GAG | ATG | GAA | GAC | ATG | GCC | GTC | 1010 |
| Leu | Phe | Leu | Ile | Ala | Gly | Lys | Ile | Leu | Glu | Met | Glu | Asp | Met | Ala | Val | |
| | | 320 | | | | | 325 | | | | | 330 | | | | |
| CTG | GGG | GGT | CAG | CTG | GGC | ATG | TAC | ACC | CTG | ACC | GTC | ATC | GTG | GGC | CTG | 1058 |
| Leu | Gly | Gly | Gln | Leu | Gly | Met | Tyr | Thr | Leu | Thr | Val | Ile | Val | Gly | Leu | |
| | 335 | | | | | 340 | | | | | 345 | | | | 350 | |
| TTC | CTC | CAT | GCC | GGC | ATT | GTC | CTT | CCC | CTC | ATC | TAC | TTC | CTC | GTC | ACT | 1106 |
| Phe | Leu | His | Ala | Gly | Ile | Val | Leu | Pro | Leu | Ile | Tyr | Phe | Leu | Val | Thr | |
| | | | | 355 | | | | | 360 | | | | | 365 | | |
| CAC | CGG | AAC | CCC | TTC | CCC | TTC | ATT | GGG | GGC | ATG | CTA | CAA | GCC | CTC | ATC | 1154 |
| His | Arg | Asn | Pro | Phe | Pro | Phe | Ile | Gly | Gly | Met | Leu | Gln | Ala | Leu | Ile | |
| | | | 370 | | | | | 375 | | | | | 380 | | | |
| ACC | GCT | ATG | GGC | ACG | TCT | TCC | AGC | TCG | GCA | ACG | CTG | CCC | ATC | ACC | TTC | 1202 |
| Thr | Ala | Met | Gly | Thr | Ser | Ser | Ser | Ser | Ala | Thr | Leu | Pro | Ile | Thr | Phe | |
| | | 385 | | | | | 390 | | | | | 395 | | | | |
| CGC | TGC | CTG | GAG | GAG | GGC | CTG | GGT | GTG | GAC | CGC | CGC | ATC | ACC | AGG | TTC | 1250 |
| Arg | Cys | Leu | Glu | Glu | Gly | Leu | Gly | Val | Asp | Arg | Arg | Ile | Thr | Arg | Phe | |
| | 400 | | | | | 405 | | | | | 410 | | | | | |
| GTC | CTG | CCC | GTG | GGC | GCC | ACG | GTC | AAC | ATG | GAT | GGC | ACT | GCC | CTC | TAC | 1298 |
| Val | Leu | Pro | Val | Gly | Ala | Thr | Val | Asn | Met | Asp | Gly | Thr | Ala | Leu | Tyr | |
| 415 | | | | | 420 | | | | | 425 | | | | | 430 | |
| GAG | GCC | CTG | GCT | GCC | ATC | TTC | ATT | GCT | CAA | GTT | AAC | AAC | TAC | GAG | CTC | 1346 |
| Glu | Ala | Leu | Ala | Ala | Ile | Phe | Ile | Ala | Gln | Val | Asn | Asn | Tyr | Glu | Leu | |
| | | | | 435 | | | | | 440 | | | | | 445 | | |
| AAC | CTG | GGT | CAG | ATC | ACA | ACC | ATC | AGC | ATC | ACG | GCC | ACA | GCA | GCC | AGT | 1394 |
| Asn | Leu | Gly | Gln | Ile | Thr | Thr | Ile | Ser | Ile | Thr | Ala | Thr | Ala | Ala | Ser | |
| | | | 450 | | | | | 455 | | | | | 460 | | | |
| GTT | GGG | GCT | GCT | GGC | ATC | CCC | CAG | GCG | GGT | CTG | GTC | ACC | ATG | GTC | ATT | 1442 |
| Val | Gly | Ala | Ala | Gly | Ile | Pro | Gln | Ala | Gly | Leu | Val | Thr | Met | Val | Ile | |
| | | 465 | | | | | 470 | | | | | 475 | | | | |
| GTG | CTT | ACG | TCG | GTC | GGC | TTG | CCC | ACG | GAA | GAC | ATC | ACG | CTC | ATC | ATC | 1490 |
| Val | Leu | Thr | Ser | Val | Gly | Leu | Pro | Thr | Glu | Asp | Ile | Thr | Leu | Ile | Ile | |
| | 480 | | | | | 485 | | | | | 490 | | | | | |
| GCC | GTG | GAC | TGG | TTC | CTT | GAC | CGG | CTT | CGC | ACA | ATG | ACC | AAC | GTA | CTG | 1538 |
| Ala | Val | Asp | Trp | Phe | Leu | Asp | Arg | Leu | Arg | Thr | Met | Thr | Asn | Val | Leu | |
| 495 | | | | | 500 | | | | | 505 | | | | | 510 | |
| GGC | CAC | TCA | ATT | GGA | GCG | GCC | GTC | ATC | GAG | CAC | TTG | TCT | CAG | CGG | GAG | 1586 |
| Gly | His | Ser | Ile | Gly | Ala | Ala | Val | Ile | Glu | His | Leu | Ser | Gln | Arg | Glu | |
| | | | | 515 | | | | | 520 | | | | | 525 | | |
| CTG | GAG | CTT | CAG | GAA | GCT | GAG | CTT | ACC | CTC | CCC | AGC | CTG | GGG | AAA | CCC | 1634 |
| Leu | Glu | Leu | Gln | Glu | Ala | Glu | Leu | Thr | Leu | Pro | Ser | Leu | Gly | Lys | Pro | |
| | | | 530 | | | | | 535 | | | | | 540 | | | |
| TAC | AAG | TCC | CTC | ATG | GCA | CAG | GAG | AAG | GGG | GCA | TCC | CGG | GGA | CGG | GGA | 1682 |
| Tyr | Lys | Ser | Leu | Met | Ala | Gln | Glu | Lys | Gly | Ala | Ser | Arg | Gly | Arg | Gly | |
| | | 545 | | | | | 550 | | | | | 555 | | | | |
| GGC | AAC | GAG | AGT | GCT | ATG | TGAGGGGCCT | | | CCAGCTCTGC | | | CCCCCCAGAG | | | AGGA | 1734 |
| Gly | Asn | Glu | Ser | Ala | Met | | | | | | | | | | | |
| | 560 | | | | | | | | | | | | | | | |

( 2 ) INFORMATION FOR SEQ ID NO:8:

( i ) SEQUENCE CHARACTERISTICS:
    ( A ) LENGTH: 564 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Met  Ser  Ser  His  Gly  Asn  Ser  Leu  Phe  Leu  Arg  Glu  Ser  Gly  Gln  Arg
 1                    5                   10                   15

Leu  Gly  Arg  Val  Gly  Trp  Leu  Gln  Arg  Leu  Gln  Glu  Ser  Leu  Gln  Gln
               20                   25                   30

Arg  Ala  Leu  Arg  Thr  Arg  Leu  Arg  Leu  Gln  Thr  Met  Thr  Leu  Glu  His
          35                   40                   45

Val  Leu  Arg  Phe  Leu  Arg  Arg  Asn  Ala  Phe  Ile  Leu  Leu  Thr  Val  Ser
     50                        55                   60

Ala  Val  Val  Ile  Gly  Val  Ser  Leu  Ala  Phe  Ala  Leu  Arg  Pro  Tyr  Gln
65                       70                   75                        80

Leu  Thr  Tyr  Arg  Gln  Ile  Lys  Tyr  Phe  Ser  Phe  Pro  Gly  Glu  Leu  Leu
                    85                   90                        95

Met  Arg  Met  Leu  Gln  Met  Leu  Val  Leu  Pro  Leu  Ile  Val  Ser  Ser  Leu
               100                  105                  110

Val  Thr  Gly  Met  Ala  Ser  Leu  Asp  Asn  Lys  Ala  Thr  Gly  Arg  Met  Gly
          115                  120                  125

Met  Arg  Ala  Ala  Val  Tyr  Tyr  Leu  Val  Thr  Thr  Ile  Ile  Ala  Val  Phe
     130                      135                  140

Ile  Gly  Ile  Leu  Met  Val  Thr  Ile  Ile  His  Pro  Gly  Lys  Gly  Ser  Lys
145                      150                  155                       160

Glu  Gly  Leu  His  Arg  Glu  Gly  Arg  Ile  Glu  Thr  Ile  Pro  Thr  Ala  Asp
                    165                  170                  175

Ala  Phe  Met  Asp  Leu  Ile  Arg  Asn  Met  Phe  Pro  Pro  Asn  Leu  Val  Glu
               180                  185                  190

Ala  Cys  Phe  Lys  Gln  Leu  Lys  Thr  Gln  Tyr  Ser  Thr  Arg  Val  Val  Thr
          195                  200                  205

Arg  Thr  Met  Val  Arg  Thr  Glu  Asn  Gly  Ser  Glu  Pro  Gly  Ala  Ser  Met
     210                      215                  220

Pro  Pro  Pro  Phe  Ser  Val  Glu  Asn  Gly  Thr  Ser  Phe  Leu  Glu  Asn  Val
225                      230                  235                       240

Thr  Arg  Ala  Leu  Gly  Thr  Leu  Gln  Glu  Met  Leu  Ser  Phe  Glu  Glu  Thr
                    245                  250                  255

Val  Pro  Val  Pro  Gly  Ser  Ala  Asn  Gly  Ile  Asn  Ala  Leu  Gly  Leu  Val
               260                  265                  270

Val  Phe  Ser  Val  Ala  Phe  Gly  Leu  Val  Ile  Gly  Gly  Met  Lys  His  Lys
          275                  280                  285

Gly  Arg  Val  Leu  Arg  Asp  Phe  Phe  Asp  Ser  Leu  Asn  Glu  Ala  Ile  Met
     290                      295                  300

Arg  Leu  Val  Gly  Ile  Ile  Ile  Trp  Tyr  Ala  Pro  Val  Gly  Ile  Leu  Phe
305                      310                  315                       320

Leu  Ile  Ala  Gly  Lys  Ile  Leu  Glu  Met  Glu  Asp  Met  Ala  Val  Leu  Gly
                    325                  330                  335

Gly  Gln  Leu  Gly  Met  Tyr  Thr  Leu  Thr  Val  Ile  Val  Gly  Leu  Phe  Leu
               340                  345                  350

His  Ala  Gly  Ile  Val  Leu  Pro  Leu  Ile  Tyr  Phe  Leu  Val  Thr  His  Arg
          355                  360                  365
```

| Asn | Pro | Phe | Pro | Phe | Ile | Gly | Gly | Met | Leu | Gln | Ala | Leu | Ile | Thr | Ala |
|---|---|---|---|---|---|---|---|---|---|---|---|---|---|---|---|
| 370 | | | | | 375 | | | | | 380 | | | | | |

| Met | Gly | Thr | Ser | Ser | Ser | Ser | Ala | Thr | Leu | Pro | Ile | Thr | Phe | Arg | Cys |
|---|---|---|---|---|---|---|---|---|---|---|---|---|---|---|---|
| 385 | | | | | 390 | | | | | 395 | | | | | 400 |

| Leu | Glu | Glu | Gly | Leu | Gly | Val | Asp | Arg | Arg | Ile | Thr | Arg | Phe | Val | Leu |
|---|---|---|---|---|---|---|---|---|---|---|---|---|---|---|---|
| | | | | 405 | | | | | 410 | | | | | 415 | |

| Pro | Val | Gly | Ala | Thr | Val | Asn | Met | Asp | Gly | Thr | Ala | Leu | Tyr | Glu | Ala |
|---|---|---|---|---|---|---|---|---|---|---|---|---|---|---|---|
| | | | 420 | | | | | 425 | | | | | 430 | | |

| Leu | Ala | Ala | Ile | Phe | Ile | Ala | Gln | Val | Asn | Asn | Tyr | Glu | Leu | Asn | Leu |
|---|---|---|---|---|---|---|---|---|---|---|---|---|---|---|---|
| | | 435 | | | | | 440 | | | | | 445 | | | |

| Gly | Gln | Ile | Thr | Thr | Ile | Ser | Ile | Thr | Ala | Thr | Ala | Ala | Ser | Val | Gly |
|---|---|---|---|---|---|---|---|---|---|---|---|---|---|---|---|
| | 450 | | | | | 455 | | | | | 460 | | | | |

| Ala | Ala | Gly | Ile | Pro | Gln | Ala | Gly | Leu | Val | Thr | Met | Val | Ile | Val | Leu |
|---|---|---|---|---|---|---|---|---|---|---|---|---|---|---|---|
| 465 | | | | | 470 | | | | | 475 | | | | | 480 |

| Thr | Ser | Val | Gly | Leu | Pro | Thr | Glu | Asp | Ile | Thr | Leu | Ile | Ile | Ala | Val |
|---|---|---|---|---|---|---|---|---|---|---|---|---|---|---|---|
| | | | | 485 | | | | | 490 | | | | | 495 | |

| Asp | Trp | Phe | Leu | Asp | Arg | Leu | Arg | Thr | Met | Thr | Asn | Val | Leu | Gly | His |
|---|---|---|---|---|---|---|---|---|---|---|---|---|---|---|---|
| | | | 500 | | | | | 505 | | | | | 510 | | |

| Ser | Ile | Gly | Ala | Ala | Val | Ile | Glu | His | Leu | Ser | Gln | Arg | Glu | Leu | Glu |
|---|---|---|---|---|---|---|---|---|---|---|---|---|---|---|---|
| | | 515 | | | | | 520 | | | | | 525 | | | |

| Leu | Gln | Glu | Ala | Glu | Leu | Thr | Leu | Pro | Ser | Leu | Gly | Lys | Pro | Tyr | Lys |
|---|---|---|---|---|---|---|---|---|---|---|---|---|---|---|---|
| | 530 | | | | | 535 | | | | | 540 | | | | |

| Ser | Leu | Met | Ala | Gln | Glu | Lys | Gly | Ala | Ser | Arg | Gly | Arg | Gly | Gly | Asn |
|---|---|---|---|---|---|---|---|---|---|---|---|---|---|---|---|
| 545 | | | | | 550 | | | | | 555 | | | | | 560 |

| Glu | Ser | Ala | Met |
|---|---|---|---|

(2) INFORMATION FOR SEQ ID NO:9:

(i) SEQUENCE CHARACTERISTICS:
        (A) LENGTH: 2194 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 189..1868

(xi) SEQUENCE DESCRIPTION: SEQ ID NO:9:

```
GAATTCCCCG TGTGGCCGCC TTAGAGGGAA GCCACACGGG CATGGCCGTG GGGCTGGCGA      60

CTGGTGTTTA GCAATCCCGA CCACCTGCCT GCTGAGGGGC TAGAGCCCTC AGCCCAGACC     120

CTGTGCCCCC GGCCGGGCTC TCATGCGTGG AATGGTGCTG TGCCCCTTGC CAGCAGGCCA     180
```

| GGCTCACC | ATG | GTG | CCG | CAT | ACC | ATC | TTG | GCA | CGG | GGG | AGG | GAC | GTG | TGC | 230 |
|---|---|---|---|---|---|---|---|---|---|---|---|---|---|---|---|
| | Met | Val | Pro | His | Thr | Ile | Leu | Ala | Arg | Gly | Arg | Asp | Val | Cys | |
| | 565 | | | | 570 | | | | | 575 | | | | | |

| AGG | CGG | AAT | GGA | CTC | CTC | ATC | CTG | TCT | GTG | CTG | TCT | GTC | ATC | GTG | GGC | 278 |
|---|---|---|---|---|---|---|---|---|---|---|---|---|---|---|---|---|
| Arg | Arg | Asn | Gly | Leu | Leu | Ile | Leu | Ser | Val | Leu | Ser | Val | Ile | Val | Gly | |
| 580 | | | | | 585 | | | | | 590 | | | | | | |

| TGC | CTC | CTC | GGC | TTC | TTC | TTG | AGG | ACC | CGG | CGC | CTC | TCA | CCA | CAG | GAA | 326 |
|---|---|---|---|---|---|---|---|---|---|---|---|---|---|---|---|---|
| Cys | Leu | Leu | Gly | Phe | Phe | Leu | Arg | Thr | Arg | Arg | Leu | Ser | Pro | Gln | Glu | |
| 595 | | | | | 600 | | | | | 605 | | | | | 610 | |

| ATT | AGT | TAC | TTC | CAG | TTC | CCC | GGA | GAG | CTC | CTG | ATG | AGG | ATG | CTG | AAG | 374 |
|---|---|---|---|---|---|---|---|---|---|---|---|---|---|---|---|---|
| Ile | Ser | Tyr | Phe | Gln | Phe | Pro | Gly | Glu | Leu | Leu | Met | Arg | Met | Leu | Lys | |
| | | | | 615 | | | | | 620 | | | | | 625 | | |

| ATG | ATG | ATC | CTG | CCA | CTG | GTG | TTC | TCC | AGC | TTG | ATG | TCC | GGA | CTT | GCC | 422 |
|---|---|---|---|---|---|---|---|---|---|---|---|---|---|---|---|---|
| Met | Met | Ile | Leu | Pro | Leu | Val | Phe | Ser | Ser | Leu | Met | Ser | Gly | Leu | Ala | |
| | | | 630 | | | | | 635 | | | | | 640 | | | |

| | | | | | | | | | | | | | | | | |
|---|---|---|---|---|---|---|---|---|---|---|---|---|---|---|---|---|
| TCC | CTG | GAT | GCC | AAG | ACC | TCT | AGC | CGC | CTG | GGC | GTC | CTC | ACC | GTG | GCG | 470 |
| Ser | Leu | Asp | Ala | Lys | Thr | Ser | Ser | Arg | Leu | Gly | Val | Leu | Thr | Val | Ala | |
| | | | 645 | | | | 650 | | | | | 655 | | | | |
| TAC | TAC | CTG | TGG | ACC | ACC | TTC | ATG | GCT | GTC | ATC | GTG | GGC | ATC | TTC | ATG | 518 |
| Tyr | Tyr | Leu | Trp | Thr | Thr | Phe | Met | Ala | Val | Ile | Val | Gly | Ile | Phe | Met | |
| | 660 | | | | | 665 | | | | | 670 | | | | | |
| GTC | TCC | ATC | ATC | CAC | CCA | GGC | AGC | GCG | GCC | CAG | AAG | GAG | ACC | ACG | GAG | 566 |
| Val | Ser | Ile | Ile | His | Pro | Gly | Ser | Ala | Ala | Gln | Lys | Glu | Thr | Thr | Glu | |
| 675 | | | | | 680 | | | | | 685 | | | | | 690 | |
| CAG | AGT | GGG | AAG | CCC | ATC | ATG | AGC | TCA | GCC | GAT | GCC | CTG | TTG | GAC | CTC | 614 |
| Gln | Ser | Gly | Lys | Pro | Ile | Met | Ser | Ser | Ala | Asp | Ala | Leu | Leu | Asp | Leu | |
| | | | | 695 | | | | 700 | | | | | 705 | | | |
| ATC | CGG | AAC | ATG | TTC | CCA | GCC | AAC | CTA | GTA | GAA | GCC | ACA | TTC | AAA | CAG | 662 |
| Ile | Arg | Asn | Met | Phe | Pro | Ala | Asn | Leu | Val | Glu | Ala | Thr | Phe | Lys | Gln | |
| | | | 710 | | | | | 715 | | | | | 720 | | | |
| TAC | CGC | ACC | AAG | ACC | ACC | CCA | GTT | GTC | AAG | TCC | CCC | AAG | GTG | GCA | CCA | 710 |
| Tyr | Arg | Thr | Lys | Thr | Thr | Pro | Val | Val | Lys | Ser | Pro | Lys | Val | Ala | Pro | |
| | | | 725 | | | | | 730 | | | | | 735 | | | |
| GAG | GAG | GCC | CCT | CCT | CGG | CGG | ATC | CTC | ATC | TAC | GGG | GTC | CAG | GAG | GAG | 758 |
| Glu | Glu | Ala | Pro | Pro | Arg | Arg | Ile | Leu | Ile | Tyr | Gly | Val | Gln | Glu | Glu | |
| | 740 | | | | | 745 | | | | | 750 | | | | | |
| AAT | GGC | TCC | CAT | GTG | CAG | AAC | TTC | GCC | CTG | GAC | CTG | ACC | CCG | CCG | CCC | 806 |
| Asn | Gly | Ser | His | Val | Gln | Asn | Phe | Ala | Leu | Asp | Leu | Thr | Pro | Pro | Pro | |
| 755 | | | | | 760 | | | | | 765 | | | | | 770 | |
| GAG | GTC | GTT | TAC | AAG | TCA | GAG | CCG | GGC | ACC | AGC | GAT | GGC | ATG | AAT | GTG | 854 |
| Glu | Val | Val | Tyr | Lys | Ser | Glu | Pro | Gly | Thr | Ser | Asp | Gly | Met | Asn | Val | |
| | | | | 775 | | | | | 780 | | | | | 785 | | |
| CTG | GGC | ATC | GTC | TTC | TTC | TCT | GCC | ACC | ATG | GGC | ATC | ATG | CTG | GGC | CGC | 902 |
| Leu | Gly | Ile | Val | Phe | Phe | Ser | Ala | Thr | Met | Gly | Ile | Met | Leu | Gly | Arg | |
| | | | 790 | | | | | 795 | | | | | 800 | | | |
| ATG | GGT | GAC | AGC | GGG | GGC | CCC | CTG | GTC | AGC | TTC | TGC | CAG | TGC | CTC | AAT | 950 |
| Met | Gly | Asp | Ser | Gly | Gly | Pro | Leu | Val | Ser | Phe | Cys | Gln | Cys | Leu | Asn | |
| | | | 805 | | | | | 810 | | | | | 815 | | | |
| GAG | TCG | GTC | ATG | AAG | ATC | GTG | GCG | GTG | GCT | GTG | TGG | TAT | TTC | CCC | TTC | 998 |
| Glu | Ser | Val | Met | Lys | Ile | Val | Ala | Val | Ala | Val | Trp | Tyr | Phe | Pro | Phe | |
| | 820 | | | | | 825 | | | | | 830 | | | | | |
| GGC | ATT | GTG | TTC | CTC | ATT | GCG | GGT | AAG | ATC | CTG | GAG | ATG | GAC | GAC | CCC | 1046 |
| Gly | Ile | Val | Phe | Leu | Ile | Ala | Gly | Lys | Ile | Leu | Glu | Met | Asp | Asp | Pro | |
| 835 | | | | | 840 | | | | | 845 | | | | | 850 | |
| AGG | GCC | GTC | GGC | AAG | AAG | CTG | GGC | TTC | TAC | TCA | GTC | ACC | GTG | GTG | TGC | 1094 |
| Arg | Ala | Val | Gly | Lys | Lys | Leu | Gly | Phe | Tyr | Ser | Val | Thr | Val | Val | Cys | |
| | | | | 855 | | | | | 860 | | | | | 865 | | |
| GGG | CTG | GTG | CTC | CAC | GGG | CTC | TTT | ATC | CTG | CCC | CTG | CTC | TAC | TTC | TTC | 1142 |
| Gly | Leu | Val | Leu | His | Gly | Leu | Phe | Ile | Leu | Pro | Leu | Leu | Tyr | Phe | Phe | |
| | | | 870 | | | | | 875 | | | | | 880 | | | |
| ATC | ACC | AAG | AAG | AAT | CCC | ATC | GTC | TTC | ATC | CGC | GGC | ATC | CTG | CAG | GCT | 1190 |
| Ile | Thr | Lys | Lys | Asn | Pro | Ile | Val | Phe | Ile | Arg | Gly | Ile | Leu | Gln | Ala | |
| | | 885 | | | | | 890 | | | | | 895 | | | | |
| CTG | CTC | ATC | GCG | CTG | GCC | ACC | TCC | TCC | AGC | TCA | GCC | ACA | CTG | CCC | ATC | 1238 |
| Leu | Leu | Ile | Ala | Leu | Ala | Thr | Ser | Ser | Ser | Ser | Ala | Thr | Leu | Pro | Ile | |
| | | 900 | | | | | 905 | | | | | 910 | | | | |
| ACC | TTC | AAG | TGC | CTG | CTG | GAG | AAC | AAC | CAC | ATC | GAC | CGG | CGC | ATC | GCT | 1286 |
| Thr | Phe | Lys | Cys | Leu | Leu | Glu | Asn | Asn | His | Ile | Asp | Arg | Arg | Ile | Ala | |
| 915 | | | | | 920 | | | | | 925 | | | | | 930 | |
| CGC | TTC | GTG | CTG | CCC | GTG | GGT | GCC | ACC | ATC | AAC | ATG | GAC | GGC | ACT | GCG | 1334 |
| Arg | Phe | Val | Leu | Pro | Val | Gly | Ala | Thr | Ile | Asn | Met | Asp | Gly | Thr | Ala | |
| | | | | 935 | | | | | 940 | | | | | 945 | | |
| CTC | TAC | GAG | GCT | GTG | GCC | GCC | ATC | TTC | ATC | GCC | CAG | GTC | AAC | AAC | TAC | 1382 |
| Leu | Tyr | Glu | Ala | Val | Ala | Ala | Ile | Phe | Ile | Ala | Gln | Val | Asn | Asn | Tyr | |
| | | | 950 | | | | | 955 | | | | | 960 | | | |

```
GAG CTG GAC TTT GGC CAG CTC ATC ACC ATC AGT ATC ACA GGC ACT GCA         1430
Glu Leu Asp Phe Gly Gln Leu Ile Thr Ile Ser Ile Thr Gly Thr Ala
            965                 970                 975

GCC AGC ATT GGG GCA GCT GGC ATC CCC CAG GCC GGC CTC GTC ACC ATG         1478
Ala Ser Ile Gly Ala Ala Gly Ile Pro Gln Ala Gly Leu Val Thr Met
            980                 985                 990

GTC ATC GTG CTC ACC TCC GTG GGA CTG CCC ACC GAT GAC ATC ACC CTC         1526
Val Ile Val Leu Thr Ser Val Gly Leu Pro Thr Asp Asp Ile Thr Leu
995                 1000                1005                1010

ATC ATT GGC GTT GAC TGG GCT CTG GAC CGT TTC CGC ACC ATG ATT AAC         1574
Ile Ile Gly Val Asp Trp Ala Leu Asp Arg Phe Arg Thr Met Ile Asn
            1015                1020                1025

GTG CTG GGT GAT GCG CTG GCA GCG GGG ATC ATG GCC CAT ATA TGT CGG         1622
Val Leu Gly Asp Ala Leu Ala Ala Gly Ile Met Ala His Ile Cys Arg
            1030                1035                1040

AAG GAT TTT GCC CGG GAC ACA GGC ACC GAG AAA CTG CTG CCC TGC GAG         1670
Lys Asp Phe Ala Arg Asp Thr Gly Thr Glu Lys Leu Leu Pro Cys Glu
            1045                1050                1055

ACC AAG CCA GTG AGC CTC CAG GAG ATC GTG GCA GCC CAG CAG AAT GGC         1718
Thr Lys Pro Val Ser Leu Gln Glu Ile Val Ala Ala Gln Gln Asn Gly
            1060                1065                1070

TGT GTG AAG AGT GTA GCC GAG GCC TCC GAG CTC ACC CTG GGC CCC ACC         1766
Cys Val Lys Ser Val Ala Glu Ala Ser Glu Leu Thr Leu Gly Pro Thr
1075                1080                1085                1090

TGC CCC CAC CAC GTC CCC GTT CAA GTG GAG CGG GAT GAG GAG CTG CCC         1814
Cys Pro His His Val Pro Val Gln Val Glu Arg Asp Glu Glu Leu Pro
            1095                1100                1105

GCT GCG AGT CTG AAC CAC TGC ACC ATC CAG ATC AGC GAG CTG GAG ACC         1862
Ala Ala Ser Leu Asn His Cys Thr Ile Gln Ile Ser Glu Leu Glu Thr
            1110                1115                1120

AAT GTC TGAGCCTGCG GAGCTGCAGG GGCAGGCGAG GCCTCCAGGG GCAGGGTCCT          1918
Asn Val

GAGGCAGGAA CTCGACTCTC CAACCCTCCT GAGCAGCCGG TAGGGGGCAG GATCACACAT       1978

TCTTCTCACC CTTGAGAGGA TGGAATTAAC CCCGCTTGGA CGGAAAATGT TTCTCAAGAG       2038

AAGGGAAAGG GTGCATGGGG GAGCCCATCC AGGGAGTGAT GGGCCCGGAT TGGCTGAAGG       2098

CCCCTTGTGA AAGTTTCCCC CGTTGTGAAC CCCGGTGAAG GGGGAAGGC AGGGGGTTTT        2158

CCGGCCCCCC TTTTCTTGGA TGATAGGATT TGGACC                                 2194
```

( 2 ) INFORMATION FOR SEQ ID NO:10:

( i ) SEQUENCE CHARACTERISTICS:
    ( A ) LENGTH: 560 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

```
Met Val Pro His Thr Ile Leu Ala Arg Gly Arg Asp Val Cys Arg Arg
1               5                   10                  15

Asn Gly Leu Leu Ile Leu Ser Val Leu Ser Val Ile Val Gly Cys Leu
            20                  25                  30

Leu Gly Phe Phe Leu Arg Thr Arg Arg Leu Ser Pro Gln Glu Ile Ser
        35                  40                  45

Tyr Phe Gln Phe Pro Gly Glu Leu Leu Met Arg Met Leu Lys Met Met
    50                  55                  60

Ile Leu Pro Leu Val Phe Ser Ser Leu Met Ser Gly Leu Ala Ser Leu
65                  70                  75                  80
```

| | | | | | | | | | | | | | | |
|---|---|---|---|---|---|---|---|---|---|---|---|---|---|---|
| Asp | Ala | Lys | Thr | Ser | Ser | Arg | Leu | Gly | Val | Leu | Thr | Val | Ala | Tyr | Tyr |
| | | | | 85 | | | | 90 | | | | | | 95 | |
| Leu | Trp | Thr | Thr | Phe | Met | Ala | Val | Ile | Val | Gly | Ile | Phe | Met | Val | Ser |
| | | | 100 | | | | | 105 | | | | | 110 | | |
| Ile | Ile | His | Pro | Gly | Ser | Ala | Ala | Gln | Lys | Glu | Thr | Thr | Glu | Gln | Ser |
| | | | 115 | | | | 120 | | | | | 125 | | | |
| Gly | Lys | Pro | Ile | Met | Ser | Ser | Ala | Asp | Ala | Leu | Leu | Asp | Leu | Ile | Arg |
| | 130 | | | | | 135 | | | | | 140 | | | | |
| Asn | Met | Phe | Pro | Ala | Asn | Leu | Val | Glu | Ala | Thr | Phe | Lys | Gln | Tyr | Arg |
| 145 | | | | | 150 | | | | | 155 | | | | | 160 |
| Thr | Lys | Thr | Thr | Pro | Val | Val | Lys | Ser | Pro | Lys | Val | Ala | Pro | Glu | Glu |
| | | | | 165 | | | | | 170 | | | | | 175 | |
| Ala | Pro | Pro | Arg | Arg | Ile | Leu | Ile | Tyr | Gly | Val | Gln | Glu | Glu | Asn | Gly |
| | | | 180 | | | | | 185 | | | | | 190 | | |
| Ser | His | Val | Gln | Asn | Phe | Ala | Leu | Asp | Leu | Thr | Pro | Pro | Pro | Glu | Val |
| | | 195 | | | | | 200 | | | | | 205 | | | |
| Val | Tyr | Lys | Ser | Glu | Pro | Gly | Thr | Ser | Asp | Gly | Met | Asn | Val | Leu | Gly |
| | 210 | | | | | 215 | | | | | 220 | | | | |
| Ile | Val | Phe | Phe | Ser | Ala | Thr | Met | Gly | Ile | Met | Leu | Gly | Arg | Met | Gly |
| 225 | | | | | 230 | | | | | 235 | | | | | 240 |
| Asp | Ser | Gly | Gly | Pro | Leu | Val | Ser | Phe | Cys | Gln | Cys | Leu | Asn | Glu | Ser |
| | | | | 245 | | | | | 250 | | | | | 255 | |
| Val | Met | Lys | Ile | Val | Ala | Val | Ala | Val | Trp | Tyr | Phe | Pro | Phe | Gly | Ile |
| | | | 260 | | | | | 265 | | | | | 270 | | |
| Val | Phe | Leu | Ile | Ala | Gly | Lys | Ile | Leu | Glu | Met | Asp | Asp | Pro | Arg | Ala |
| | | 275 | | | | | 280 | | | | | 285 | | | |
| Val | Gly | Lys | Lys | Leu | Gly | Phe | Tyr | Ser | Val | Thr | Val | Val | Cys | Gly | Leu |
| | 290 | | | | | 295 | | | | | 300 | | | | |
| Val | Leu | His | Gly | Leu | Phe | Ile | Leu | Pro | Leu | Leu | Tyr | Phe | Phe | Ile | Thr |
| 305 | | | | | 310 | | | | | 315 | | | | | 320 |
| Lys | Lys | Asn | Pro | Ile | Val | Phe | Ile | Arg | Gly | Ile | Leu | Gln | Ala | Leu | Leu |
| | | | | 325 | | | | | 330 | | | | | 335 | |
| Ile | Ala | Leu | Ala | Thr | Ser | Ser | Ser | Ala | Thr | Leu | Pro | Ile | Thr | Phe |
| | | | 340 | | | | | 345 | | | | | 350 | | |
| Lys | Cys | Leu | Leu | Glu | Asn | Asn | His | Ile | Asp | Arg | Arg | Ile | Ala | Arg | Phe |
| | | | 355 | | | | | 360 | | | | | 365 | | |
| Val | Leu | Pro | Val | Gly | Ala | Thr | Ile | Asn | Met | Asp | Gly | Thr | Ala | Leu | Tyr |
| | | 370 | | | | | 375 | | | | | 380 | | | |
| Glu | Ala | Val | Ala | Ala | Ile | Phe | Ile | Ala | Gln | Val | Asn | Asn | Tyr | Glu | Leu |
| 385 | | | | | 390 | | | | | 395 | | | | | 400 |
| Asp | Phe | Gly | Gln | Leu | Ile | Thr | Ile | Ser | Ile | Thr | Gly | Thr | Ala | Ala | Ser |
| | | | | 405 | | | | | 410 | | | | | 415 | |
| Ile | Gly | Ala | Ala | Gly | Ile | Pro | Gln | Ala | Gly | Leu | Val | Thr | Met | Val | Ile |
| | | | 420 | | | | | 425 | | | | | 430 | | |
| Val | Leu | Thr | Ser | Val | Gly | Leu | Pro | Thr | Asp | Asp | Ile | Thr | Leu | Ile | Ile |
| | | 435 | | | | | 440 | | | | | 445 | | | |
| Gly | Val | Asp | Trp | Ala | Leu | Asp | Arg | Phe | Arg | Thr | Met | Ile | Asn | Val | Leu |
| | 450 | | | | | 455 | | | | | 460 | | | | |
| Gly | Asp | Ala | Leu | Ala | Ala | Gly | Ile | Met | Ala | His | Ile | Cys | Arg | Lys | Asp |
| 465 | | | | | 470 | | | | | 475 | | | | | 480 |
| Phe | Ala | Arg | Asp | Thr | Gly | Thr | Glu | Lys | Leu | Leu | Pro | Cys | Glu | Thr | Lys |
| | | | | 485 | | | | | 490 | | | | | 495 | |
| Pro | Val | Ser | Leu | Gln | Glu | Ile | Val | Ala | Ala | Gln | Gln | Asn | Gly | Cys | Val |

```
                          500                       505                        510
Lys  Ser  Val  Ala  Glu  Ala  Ser  Glu  Leu  Thr  Leu  Gly  Pro  Thr  Cys  Pro
               515                      520                      525

His  His  Val  Pro  Val  Gln  Val  Glu  Arg  Asp  Glu  Glu  Leu  Pro  Ala  Ala
          530                      535                      540

Ser  Leu  Asn  His  Cys  Thr  Ile  Gln  Ile  Ser  Glu  Leu  Glu  Thr  Asn  Val
545                      550                      555                      560
```

( 2 ) INFORMATION FOR SEQ ID NO:11:

( i ) SEQUENCE CHARACTERISTICS:
        ( A ) LENGTH: 1912 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 83..1774

( x i ) SEQUENCE DESCRIPTION: SEQ ID NO:11:

```
GAATTCGCGG  CCGCGTCGAC  GGAACCCCGG  CGCCCTGTCT  CAATGGGCAG  CGGGCCCACC         60

CCCAAGGACC  ACTGAGGACG  CC ATG GCG GTG ACT GTG GAC GCG ATG CTG GCT           112
                          Met Ala Val Thr Val Asp Ala Met Leu Ala
                                              565                 570

CGC  GCC  AAG  GAT  GTC  TGT  AAG  AGG  AAC  GGC  CTG  CTC  ATC  TTG  TCC  GTC   160
Arg  Ala  Lys  Asp  Val  Cys  Lys  Arg  Asn  Gly  Leu  Leu  Ile  Leu  Ser  Val
               575                      580                      585

TTG  TCC  GTC  ATC  ATA  GGG  TGT  CTG  CTG  GGG  TTC  TTC  CTG  AGG  ACT  CGT   208
Leu  Ser  Val  Ile  Ile  Gly  Cys  Leu  Leu  Gly  Phe  Phe  Leu  Arg  Thr  Arg
               590                      595                      600

CGC  CTG  TGT  GAG  CAG  GAA  ATA  AGC  TAC  TTC  CAG  TTT  CCT  GGA  GAG  CTG   256
Arg  Leu  Cys  Glu  Gln  Glu  Ile  Ser  Tyr  Phe  Gln  Phe  Pro  Gly  Glu  Leu
               605                      610                      615

CTG  ATG  AGG  ATG  CTG  AAG  ATG  CTG  ATT  CTC  CCG  CTG  GTC  GTC  TCA  AGC   304
Leu  Met  Arg  Met  Leu  Lys  Met  Leu  Ile  Leu  Pro  Leu  Val  Val  Ser  Ser
620                      625                      630

TTA  ATG  TCA  GGG  TTG  GCG  GCC  TTG  GAT  GCC  AAG  ACT  TCC  AGC  CGG  CTC   352
Leu  Met  Ser  Gly  Leu  Ala  Ala  Leu  Asp  Ala  Lys  Thr  Ser  Ser  Arg  Leu
635                      640                      645                      650

GGC  ATC  ATA  ACC  ATC  GCT  TAC  TAC  CTG  TGG  ACG  ACC  TTT  GTG  GCA  GTC   400
Gly  Ile  Ile  Thr  Ile  Ala  Tyr  Tyr  Leu  Trp  Thr  Thr  Phe  Val  Ala  Val
               655                      660                      665

ATA  GTG  GGG  ATT  GTC  ATG  GTC  TCC  ATA  ATT  CAC  CCT  GGA  GGA  GCG  GCC   448
Ile  Val  Gly  Ile  Val  Met  Val  Ser  Ile  Ile  His  Pro  Gly  Gly  Ala  Ala
               670                      675                      680

CAG  AAG  GAG  AAC  ACC  GAC  CAG  AGT  GGG  AAG  CCC  ATC  ATG  AGC  TCC  GCC   496
Gln  Lys  Glu  Asn  Thr  Asp  Gln  Ser  Gly  Lys  Pro  Ile  Met  Ser  Ser  Ala
               685                      690                      695

GAT  GCC  TTA  CTA  GAC  CTC  ATT  AGG  AAT  ATG  TTT  CCA  GCT  AAC  CTT  GTT   544
Asp  Ala  Leu  Leu  Asp  Leu  Ile  Arg  Asn  Met  Phe  Pro  Ala  Asn  Leu  Val
          700                      705                      710

GAA  GCT  ACA  TTT  AAA  CAG  TAC  CGT  ACC  AAG  AAC  ACT  CCC  ATT  GTC  AAA   592
Glu  Ala  Thr  Phe  Lys  Gln  Tyr  Arg  Thr  Lys  Asn  Thr  Pro  Ile  Val  Lys
715                      720                      725                      730

ACC  GGT  AAG  GTG  CCT  CCT  TCT  GAA  AGC  ATC  ACC  CAT  CGG  ATC  CTA  GTC   640
Thr  Gly  Lys  Val  Pro  Pro  Ser  Glu  Ser  Ile  Thr  His  Arg  Ile  Leu  Val
                         735                      740                      745

TAC  GGG  ATC  CAG  GAT  GAG  AAT  GGA  TCA  AAC  ATC  CAG  AAC  TTT  GCA  CTG   688
Tyr  Gly  Ile  Gln  Asp  Glu  Asn  Gly  Ser  Asn  Ile  Gln  Asn  Phe  Ala  Leu
```

|  |  |  |  |  |  |  |  |  |  |  |  |  |  |  |  |  |
|---|---|---|---|---|---|---|---|---|---|---|---|---|---|---|---|---|
|  |  |  |  | 750 |  |  |  |  | 755 |  |  |  |  | 760 |  |  |
| GAC | ATC | ACG | CCA | CCG | CCA | GAG | GTG | ATC | TAC | AAA | TCT | GAG | CCT | GGC | ACC | 736 |
| Asp | Ile | Thr | Pro | Pro | Pro | Glu | Val | Ile | Tyr | Lys | Ser | Glu | Pro | Gly | Thr |  |
|  |  | 765 |  |  |  | 770 |  |  |  | 775 |  |  |  |  |  |  |
| AGC | GAA | GGC | ATG | AAT | GTG | CTG | GGC | ATT | GTG | ATC | TTC | TCT | GCA | ACG | ATG | 784 |
| Ser | Glu | Gly | Met | Asn | Val | Leu | Gly | Ile | Val | Ile | Phe | Ser | Ala | Thr | Met |  |
|  | 780 |  |  |  |  | 785 |  |  |  |  | 790 |  |  |  |  |  |
| GGA | ATA | ATG | CTG | GGG | AGA | ATG | GGC | ACC | AGC | GGG | GTC | CCG | GTG | GTC | AGC | 832 |
| Gly | Ile | Met | Leu | Gly | Arg | Met | Gly | Thr | Ser | Gly | Val | Pro | Val | Val | Ser |  |
| 795 |  |  |  |  | 800 |  |  |  |  | 805 |  |  |  |  | 810 |  |
| TTC | TGC | CAG | TGT | CTG | AAT | GAA | TCT | GTG | ATG | AAG | ATA | GTG | GCT | GTC | TCC | 880 |
| Phe | Cys | Gln | Cys | Leu | Asn | Glu | Ser | Val | Met | Lys | Ile | Val | Ala | Val | Ser |  |
|  |  |  |  | 815 |  |  |  |  | 820 |  |  |  |  | 825 |  |  |
| GTG | TGG | TAT | TTC | CCA | TTT | GGC | ATC | GTA | TTC | CTC | ATT | GCA | GGA | AAG | ATA | 928 |
| Val | Trp | Tyr | Phe | Pro | Phe | Gly | Ile | Val | Phe | Leu | Ile | Ala | Gly | Lys | Ile |  |
|  |  |  | 830 |  |  |  |  | 835 |  |  |  |  | 840 |  |  |  |
| TTG | GAG | ATG | GAT | GAC | CCA | ACA | GCC | TTC | GGG | AAG | AAA | CTG | GGC | TTT | TAC | 976 |
| Leu | Glu | Met | Asp | Asp | Pro | Thr | Ala | Phe | Gly | Lys | Lys | Leu | Gly | Phe | Tyr |  |
|  |  | 845 |  |  |  |  | 850 |  |  |  |  | 855 |  |  |  |  |
| GCC | ATC | ACT | GTG | GTT | TGT | GGC | TTG | GTC | GTG | CAT | GGA | CTT | TTC | ATT | CTG | 1024 |
| Ala | Ile | Thr | Val | Val | Cys | Gly | Leu | Val | Val | His | Gly | Leu | Phe | Ile | Leu |  |
|  | 860 |  |  |  |  | 865 |  |  |  |  | 870 |  |  |  |  |  |
| CCA | ATG | ATG | TAT | CTC | TTC | ATC | ACC | AAG | AAA | AAC | CCC | ATT | GTC | TTC | ATC | 1072 |
| Pro | Met | Met | Tyr | Leu | Phe | Ile | Thr | Lys | Lys | Asn | Pro | Ile | Val | Phe | Ile |  |
| 875 |  |  |  |  | 880 |  |  |  |  | 885 |  |  |  |  | 890 |  |
| CGG | GGG | GTT | CTT | CAA | GCC | TTG | CTC | ATA | GCT | CTG | GCC | ACG | TCA | TCC | AGC | 1120 |
| Arg | Gly | Val | Leu | Gln | Ala | Leu | Leu | Ile | Ala | Leu | Ala | Thr | Ser | Ser | Ser |  |
|  |  |  |  | 895 |  |  |  |  | 900 |  |  |  |  | 905 |  |  |
| TCG | GCC | ACA | TTG | CCT | ATA | ACC | TTC | AAG | TGT | TTG | CTG | GAG | AAT | AAT | CAC | 1168 |
| Ser | Ala | Thr | Leu | Pro | Ile | Thr | Phe | Lys | Cys | Leu | Leu | Glu | Asn | Asn | His |  |
|  |  |  | 910 |  |  |  |  | 915 |  |  |  |  | 920 |  |  |  |
| ATT | GAC | AGA | AGG | ATT | GCC | AGG | TTT | GTG | CTG | CCT | GTG | GGA | GCC | ACC | ATT | 1216 |
| Ile | Asp | Arg | Arg | Ile | Ala | Arg | Phe | Val | Leu | Pro | Val | Gly | Ala | Thr | Ile |  |
|  |  | 925 |  |  |  | 930 |  |  |  |  | 935 |  |  |  |  |  |
| AAC | ATG | GAT | GGA | ACC | GCT | CTT | TAT | GAA | GCC | GTG | GCG | GCC | ATC | TTT | ATT | 1264 |
| Asn | Met | Asp | Gly | Thr | Ala | Leu | Tyr | Glu | Ala | Val | Ala | Ala | Ile | Phe | Ile |  |
|  | 940 |  |  |  |  | 945 |  |  |  |  | 950 |  |  |  |  |  |
| GCT | CAA | GTG | AAC | AAC | TAT | GAA | CTA | GAC | TTT | GGG | CAG | ATT | ATT | ACC | ATA | 1312 |
| Ala | Gln | Val | Asn | Asn | Tyr | Glu | Leu | Asp | Phe | Gly | Gln | Ile | Ile | Thr | Ile |  |
| 955 |  |  |  |  | 960 |  |  |  |  | 965 |  |  |  |  | 970 |  |
| AGC | ATC | ACA | GCA | ACA | GCC | GCC | AGT | ATC | GGG | GCA | GCG | GGC | ATT | CCA | CAG | 1360 |
| Ser | Ile | Thr | Ala | Thr | Ala | Ala | Ser | Ile | Gly | Ala | Ala | Gly | Ile | Pro | Gln |  |
|  |  |  |  | 975 |  |  |  |  | 980 |  |  |  |  | 985 |  |  |
| GCT | GGC | CTT | GTG | ACA | ATG | GTC | ATC | GTG | CTC | ACA | TCA | GTC | GGG | CTA | CCT | 1408 |
| Ala | Gly | Leu | Val | Thr | Met | Val | Ile | Val | Leu | Thr | Ser | Val | Gly | Leu | Pro |  |
|  |  |  | 990 |  |  |  |  | 995 |  |  |  |  | 1000 |  |  |  |
| ACC | GAT | GAC | ATC | ACT | CTC | ATC | ATC | GCT | GTG | GAC | TGG | GCA | CTA | GAT | CGA | 1456 |
| Thr | Asp | Asp | Ile | Thr | Leu | Ile | Ile | Ala | Val | Asp | Trp | Ala | Leu | Asp | Arg |  |
|  |  | 1005 |  |  |  | 1010 |  |  |  |  | 1015 |  |  |  |  |  |
| TTT | AGA | ACA | ATG | ATC | AAC | GTC | TTG | GGA | GAT | GCC | TTG | GCT | GCT | GGG | ATC | 1504 |
| Phe | Arg | Thr | Met | Ile | Asn | Val | Leu | Gly | Asp | Ala | Leu | Ala | Ala | Gly | Ile |  |
|  | 1020 |  |  |  |  | 1025 |  |  |  |  | 1030 |  |  |  |  |  |
| ATG | GCT | CAC | ATC | TGC | AGA | AAG | GAT | TTT | GAA | AAC | CAG | AAC | GAT | GAG | GTT | 1552 |
| Met | Ala | His | Ile | Cys | Arg | Lys | Asp | Phe | Glu | Asn | Gln | Asn | Asp | Glu | Val |  |
| 1035 |  |  |  |  | 1040 |  |  |  |  | 1045 |  |  |  |  | 1050 |  |
| CCA | CTG | ATC | TGT | GAA | ACG | AAA | AAT | TTT | AGC | ATC | CAC | CAA | ATC | ATG | GCG | 1600 |
| Pro | Leu | Ile | Cys | Glu | Thr | Lys | Asn | Phe | Ser | Ile | His | Gln | Ile | Met | Ala |  |
|  |  |  |  |  | 1055 |  |  |  |  | 1060 |  |  |  |  | 1065 |  |
| TAC | CAG | AGA | AAC | GGC | TGC | GTG | AAA | AAT | ATG | AAC | GCT | TAT | CAC | GGG | CAG | 1648 |
| Tyr | Gln | Arg | Asn | Gly | Cys | Val | Lys | Asn | Met | Asn | Ala | Tyr | His | Gly | Gln |  |

-continued

```
                  1070                      1075                     1080
GAG  ACA  GTG  AAA  GAC  TGT  CAT  TAC  ATA  GAC  ATG  GAG  CCG  GAA  GGT  GCC      1696
Glu  Thr  Val  Lys  Asp  Cys  His  Tyr  Ile  Asp  Met  Glu  Pro  Glu  Gly  Ala
          1085                    1090                    1095

CCG  GAG  GAG  AAC  CAC  ATT  GAG  GTA  TCC  AAC  GAC  AAG  GAC  CAC  TGC  ACC      1744
Pro  Glu  Glu  Asn  His  Ile  Glu  Val  Ser  Asn  Asp  Lys  Asp  His  Cys  Thr
     1100                    1105                    1110

ATT  GAG  ATC  AAT  GAA  GTT  GAA  ACA  AAC  GTG  TAGCTGATTG  CCATGCAAAC            1794
Ile  Glu  Ile  Asn  Glu  Val  Glu  Thr  Asn  Val
1115                    1120

CTCATCTGCT  ACTGGAGAGG  GGACAATGGT  GGCAGAACCA  GCAGCTCTGA  GTAAATAAGG              1854

CCCTAAAGAT  GACAGACTCG  ACAATTGTGC  ATTTATCTGA  GGCACAAATT  CATTAAGG                1912
```

( 2 ) INFORMATION FOR SEQ ID NO:12:

( i ) SEQUENCE CHARACTERISTICS:
      ( A ) LENGTH: 564 amino acids
      ( B ) TYPE: amino acid
      ( D ) TOPOLOGY: linear ( i i ) MOLECULE TYPE: protein ( x i ) SEQUENCE DESCRIPTION: SEQ ID NO:12:

```
Met  Ala  Val  Thr  Val  Asp  Ala  Met  Leu  Ala  Arg  Ala  Lys  Asp  Val  Cys
 1              5                        10                       15

Lys  Arg  Asn  Gly  Leu  Leu  Ile  Leu  Ser  Val  Leu  Ser  Val  Ile  Ile  Gly
               20                        25                       30

Cys  Leu  Leu  Gly  Phe  Phe  Leu  Arg  Thr  Arg  Arg  Leu  Cys  Glu  Gln  Glu
          35                        40                       45

Ile  Ser  Tyr  Phe  Gln  Phe  Pro  Gly  Glu  Leu  Leu  Met  Arg  Met  Leu  Lys
     50                        55                       60

Met  Leu  Ile  Leu  Pro  Leu  Val  Val  Ser  Ser  Leu  Met  Ser  Gly  Leu  Ala
65                        70                       75                       80

Ala  Leu  Asp  Ala  Lys  Thr  Ser  Ser  Arg  Leu  Gly  Ile  Ile  Thr  Ile  Ala
                85                        90                       95

Tyr  Tyr  Leu  Trp  Thr  Thr  Phe  Val  Ala  Val  Ile  Val  Gly  Ile  Val  Met
               100                       105                      110

Val  Ser  Ile  Ile  His  Pro  Gly  Gly  Ala  Ala  Gln  Lys  Glu  Asn  Thr  Asp
          115                       120                      125

Gln  Ser  Gly  Lys  Pro  Ile  Met  Ser  Ser  Ala  Asp  Ala  Leu  Leu  Asp  Leu
     130                       135                      140

Ile  Arg  Asn  Met  Phe  Pro  Ala  Asn  Leu  Val  Glu  Ala  Thr  Phe  Lys  Gln
145                       150                      155                      160

Tyr  Arg  Thr  Lys  Asn  Thr  Pro  Ile  Val  Lys  Thr  Gly  Lys  Val  Pro  Pro
                165                       170                      175

Ser  Glu  Ser  Ile  Thr  His  Arg  Ile  Leu  Val  Tyr  Gly  Ile  Gln  Asp  Glu
               180                       185                      190

Asn  Gly  Ser  Asn  Ile  Gln  Asn  Phe  Ala  Leu  Asp  Ile  Thr  Pro  Pro  Pro
          195                       200                      205

Glu  Val  Ile  Tyr  Lys  Ser  Glu  Pro  Gly  Thr  Ser  Glu  Gly  Met  Asn  Val
     210                       215                      220

Leu  Gly  Ile  Val  Ile  Phe  Ser  Ala  Thr  Met  Gly  Ile  Met  Leu  Gly  Arg
225                       230                      235                      240

Met  Gly  Thr  Ser  Gly  Val  Pro  Val  Val  Ser  Phe  Cys  Gln  Cys  Leu  Asn
                245                       250                      255

Glu  Ser  Val  Met  Lys  Ile  Val  Ala  Val  Ser  Val  Trp  Tyr  Phe  Pro  Phe
               260                       265                      270
```

| | | | | | | | | | | | | | |
|---|---|---|---|---|---|---|---|---|---|---|---|---|---|
| Gly | Ile | Val | Phe | Leu | Ile | Ala | Gly | Lys | Ile | Leu | Glu | Met | Asp | Asp | Pro |
| | | 275 | | | | | 280 | | | | 285 | | | |
| Thr | Ala | Phe | Gly | Lys | Lys | Leu | Gly | Phe | Tyr | Ala | Ile | Thr | Val | Val | Cys |
| | 290 | | | | 295 | | | | | 300 | | | | |
| Gly | Leu | Val | Val | His | Gly | Leu | Phe | Ile | Leu | Pro | Met | Met | Tyr | Leu | Phe |
| 305 | | | | | 310 | | | | | 315 | | | | | 320 |
| Ile | Thr | Lys | Lys | Asn | Pro | Ile | Val | Phe | Ile | Arg | Gly | Val | Leu | Gln | Ala |
| | | | | 325 | | | | | 330 | | | | | 335 | |
| Leu | Leu | Ile | Ala | Leu | Ala | Thr | Ser | Ser | Ser | Ala | Thr | Leu | Pro | Ile |
| | | | 340 | | | | | 345 | | | | 350 | | |
| Thr | Phe | Lys | Cys | Leu | Leu | Glu | Asn | Asn | His | Ile | Asp | Arg | Arg | Ile | Ala |
| | | 355 | | | | | 360 | | | | | 365 | | | |
| Arg | Phe | Val | Leu | Pro | Val | Gly | Ala | Thr | Ile | Asn | Met | Asp | Gly | Thr | Ala |
| | 370 | | | | | 375 | | | | | 380 | | | | |
| Leu | Tyr | Glu | Ala | Val | Ala | Ala | Ile | Phe | Ile | Ala | Gln | Val | Asn | Asn | Tyr |
| 385 | | | | | 390 | | | | | 395 | | | | | 400 |
| Glu | Leu | Asp | Phe | Gly | Gln | Ile | Ile | Thr | Ile | Ser | Ile | Thr | Ala | Thr | Ala |
| | | | | 405 | | | | | 410 | | | | | 415 | |
| Ala | Ser | Ile | Gly | Ala | Ala | Gly | Ile | Pro | Gln | Ala | Gly | Leu | Val | Thr | Met |
| | | | 420 | | | | | 425 | | | | | 430 | | |
| Val | Ile | Val | Leu | Thr | Ser | Val | Gly | Leu | Pro | Thr | Asp | Asp | Ile | Thr | Leu |
| | | 435 | | | | | 440 | | | | | 445 | | | |
| Ile | Ile | Ala | Val | Asp | Trp | Ala | Leu | Asp | Arg | Phe | Arg | Thr | Met | Ile | Asn |
| | 450 | | | | | 455 | | | | | 460 | | | | |
| Val | Leu | Gly | Asp | Ala | Leu | Ala | Ala | Gly | Ile | Met | Ala | His | Ile | Cys | Arg |
| 465 | | | | | 470 | | | | | 475 | | | | | 480 |
| Lys | Asp | Phe | Glu | Asn | Gln | Asn | Asp | Glu | Val | Pro | Leu | Ile | Cys | Glu | Thr |
| | | | | 485 | | | | | 490 | | | | | 495 | |
| Lys | Asn | Phe | Ser | Ile | His | Gln | Ile | Met | Ala | Tyr | Gln | Arg | Asn | Gly | Cys |
| | | | 500 | | | | | 505 | | | | | 510 | | |
| Val | Lys | Asn | Met | Asn | Ala | Tyr | His | Gly | Gln | Glu | Thr | Val | Lys | Asp | Cys |
| | | 515 | | | | | 520 | | | | | 525 | | | |
| His | Tyr | Ile | Asp | Met | Glu | Pro | Glu | Gly | Ala | Pro | Glu | Glu | Asn | His | Ile |
| | 530 | | | | | 535 | | | | | 540 | | | | |
| Glu | Val | Ser | Asn | Asp | Lys | Asp | His | Cys | Thr | Ile | Glu | Ile | Asn | Glu | Val |
| 545 | | | | | 550 | | | | | 555 | | | | | 560 |
| Glu | Thr | Asn | Val | | | | | | | | | | | | |

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CGCGGGTACC  CTACCATGGT  GCCGCAT                                     27

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CGCGTCTAGA GGCTCAGACA TTGGTCTC 2 8

EXCITATORY AMINO ACID TRANSPORTER GENE AND USES

This application claims priority to U.S. Provisional Patent Application Ser. No. 60/028,325, filed Oct. 11, 1996.

This application is also a continuation-in-part of U.S. Ser. No. 08/140,729, filed Oct. 20, 1993, now U.S. Pat. No. 5,658,782, issued Aug. 19, 1997, which is incorporated by reference herein its entirety.

This invention was made with government support under National Institute of Health grant DA07595. The government has certain rights to this invention.

BACKGROUND OF THE INVENTION

1. Field of the Invention

This invention relates to amino transporters form mammalian species and the genes corresponding to such transporters. Specifically, the invention relates to the isolation, cloning and sequencing of complementary DNA (cDNA) copies of messenger RNA (mRNA) encoding a novel human amino acid transporter gene. The invention also relates to the construction of recombinant expression constructs comprising such cDNAs from a novel human amino acid transporter gene of the invention, said recombinant expression constructs being capable of expressing amino acid transporter protein in cultures of transformed prokaryotic and eukaryotic cells as well as in amphibian oocytes. Production of the transporter protein of the invention in such cultures and oocytes is also provided. The invention relates to the use of cultures of such transformed cells to produce homogeneous compositions of the novel transporter protein. The invention also provides cultures of such cells and oocytes expressing transporter protein for the characterization of novel and useful drugs. Antibodies against and epitopes of the transporter protein are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organism such as man. For these reasons, specialized trans-membrane transporter proteins have evolved in all organisms to recover or scavenge extracellular amino acids (see Christensen, 1990, *Physiol. Rev.* 70: 43–77 for review).

These transporter proteins play a particularly important role in uptake of extracellular amino acids in the vertebrate brain and peripheral motor and sensory tissues (see Nicholls & Attwell, 1990, TIPS 11: 462–468). Amino acids that function as neurotransmitters must be scavenged form the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS: see Pines et al., 1992 *Nature* 360: 464–467).

Glutamate is one example of such amino acid. Glutamate is an excitatory neurotransmitter (i.e., excitatory neurons use glutamate as a neurotransmitter). When present in excess (>about 300 $\mu$M; Bouvier et al., 1992, *Nature* 360: 471–474; Nicholls & Attwell, ibid.; >5 $\mu$M for 5 min.; Choi et al., 1987, *J. Neurosci.* 7: 357–358), extracellular glutamate causes neuronal cell death. Glutamate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather that decreasing the amount of extracellular glutamate found in the brain. The resulting high extracellular concentration of glutamate causes neuron death, with extremely deleterious consequences for motor and other brain functions, resulting in stroke and other instances of organic brain dysfunction.

This important role for amino acid transporters in maintaining brain homeostasis of extracellular amino acid concentrations has provided the impetus for the search for an development of compounds to modulate and control transporter function. However, conventional screening methods require the use of animal brain slices in binding assays as a first step. This is suboptimal for a number of reasons, including interference in the binding assay by non-specific binding of heterologous (i.e.., non-transporter) cell surface proteins expressed by brain cells in such slices; differential binding by cells other than neuronal cells present in the brain slice, such as glial cells or blood cells; and the possibility that putative drug binding behavior in animal brain cells will differ form the binding behavior in human brain cells in subtle but critical ways. These same limitations arise in the use of animal-derived sensory tissue, particularly retina, to study the effects of transporter function in these tissues. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, *J. Biol. Chem.* 242: 5237–5246 report the discovery of a neutral amino acid transporter (termed the ACS transporter) in Erlich ascites tumor cells.

Makowske & Christensen, 1982, *J. Biol Chem.* 257: 14635–14638 provide a biochemical characterization of hepatic amino acid transport.

Kanner & Schuldiner, 1987, CRC *Crit. Rev. Biochem.* 22: 1–38 provide a review of the biochemistry of neurotransmitters.

Olney et al., 1990 *Science* 248: 596–599 disclose that the amino acid cysteine is a neurotoxin when present in excess extracellularly.

Wallace et al., 1990, *J. Bacteriol.* 172: 3214–3220 report the cloning and sequencing of a glutamate/aspartate transporter gene termed gltP from *Escherichia coli* strain K12.

Kim et al., 1991, *Nature* 352: 725–728 report the discovery that a cationic amino acid transporter is the cell surface target for infection by ecotropic retroviruses in mice.

Wang et al., 1991, *Nature* 352: 729–731 report the discovery that a cationic amino acid transporter is the cell surface target for infection by ecotropic retroviruses in mice.

Maenz et al., 1992, *J. Biol Chem.* 267: 8330–8335 report that the ASC transporter acts in a electrochemically neutral manner so that sodium ion co-transport occurs without disrupting the normal membrane potential of the cells expressing the transporter.

Engelke et al., 1992, *J Bacteriol.* 171: 5551–5560 report cloning of a dicarboxylate carrier from *Rhizobium meliloti*.

Guastella et al., 1992, *Proc. Natl. Acad. Sci.* USA 89: 7189–7193 disclose the cloning of a sodium ion and chloride ion-dependent glycine transporter from a glioma cell line that is expressed in the rat forebrain and cerebellum.

Kavanaugh et al., 1992, *J Biol Chem.* 267: 22007–22009 report that biochemical characterization of a rat brain GABA transporter expressed in vitro in *Xenopus laevis* oocytes.

Storck et al., 1992, *Proc. Natl. Acad. Sci.* USA 89: 10955–10959 disclose the cloning and sequencing of a sodium ion-dependent glutamate/aspartate transporter from rat brain termed GLAST1.

Bouvier et al., *ibid.*, disclose the biochemical characterization of a glial cell-derived glutamate transporter.

Pines et al., *ibid.*, report the cloning and sequencing of a glial cell glutamate transporter from rat brain termed GLT-1.

Kanai & Hediger, 1992, *Nature* 360: 467–471 disclose the cloning and sequence of a sodium ion-dependent neutral amino acid transporter of the A type that is homologous to a sodium-ion dependent glucose transporter.

Arriza et al., 1994, *J Neurosci.* 14: 5559–5569 disclose genes for three novel glutamate transporters.

Nicholls & Attwell, *ibid.*, review the role of amino acids and amino acid transporters in normal and pathological brain functions.

In humans, the sodium-dependent glutamate uptake transporters include 4 known subtypes, termed EAAT1 through EAAT3, that are expressed in neurons in the brain, as disclosed in co-owned and co-pending U.S. Ser. No. 08/140,729, filed Oct. 23, 1993, now U.S. Pat. No. 5,658,782, issued Aug. 19, 1997, and EAAT4, that are expressed in neurons in the cerebellum, as disclosed in co-owned and co-pending U.S. Ser. No. 08/663,808, filed Jun. 14, 1996, the disclosures of each of which are incorporated by reference herein. The transport of glutamate is driven by the co-transport of sodium ions and counter-transport of potassium ions down their electrochemical gradients across mammalian cell membranes, and may also involve co-transport of a proton. In addition, glutamate transport is also associated with uncoupled, passive efflux of chloride ions, the relative magnitude of such efflux varying with EAAT subtype. For EAAT1 through EAAT3, the magnitude of the chloride conductance is similar or smaller than the electrogenic transport current; for EAAT4, on the other hand, the current generated in experimental systems using *Xenopus laevis* oocytes is almost entirely due to chloride ion flux.

A chloride ion current associated with glutamate transporter activity has also been observed in retina, specifically retinal cone and rod photoreceptor cells and bipolar cells. As in central nervous system tissues, glutamate transport may play an important role in several neurological diseases that occur in the eye. Excessive levels of glutamate are neurotoxic and may be responsible for damage to retinal neurons due to glaucoma (Dreyer et al., 1996, *Arch. Ophthalmol.* 114: 299–305) and retinal ischemia (Honda, 1996, *Nippon Ganka Gakkat Zasshi* 100: 937–955), as well as retinopathy associated with premature birth, hypertension and diabetes (Kalloniatis, 1995, *J. Amer. Optom. Assoc.* 66: 750–757). Up-regulation of glutamate transport could be neuroprotective by lowering extracellular levels of glutamate in retina; pharmacological regulation of glutamate transporters has been demonstrated in frog oocytes (Zerangue et al., 1995, *J. Biol. Chem.* 270: 6433–6435) and native cells (Kataoka et al., 1997, *J. Neurosci.* 17: 7017–7024). Thus, there is a need in the art to determine the basis of the chloride ion current in retinal tissues and to determine whether the activity of a EAAT transporter is involved, in order to develop retinal protective agents for a variety of diseases and disorders.

SUMMARY OF THE INVENTION

The present invention relates to the cloning, expression and functional characterization of mammalian excitatory amino acid transporter genes. The invention comprises nucleic acids having a nucleotide sequence of a novel excitatory amino acid transporter gene. The nucleic acids provided by the invention each comprise a complementary DNA (cDNA) copy of the corresponding mRNA transcribed in vivo from the excitatory amino acid transporter gene of the invention. Also provided is the deduced amino acid sequences of the cognate protein of the cDNA provided by the invention.

This invention provides nucleic acids, nucleic acid hybridization probes, recombinant eukaryotic expression constructs capable of expressing the excitatory amino acid transporter of the invention in cultures of transformed cells and in amphibian oocytes, such as cultures of transformed eukaryotic cells and such amphibian oocytes that synthesize the excitatory amino acid transporter of the invention, and a homogeneous composition of the excitatory amino acid transporter protein of the invention. Methods for characterizing this transporter protein and methods for using this protein and cells and oocytes expressing this protein for the development of agents having pharmacological uses related to this transporter protein are also provided by the invention.

In a first aspect, the invention provides a nucleic acid having a nucleotide sequence encoding a human excitatory amino acid transporter that is the EAAT5 transporter. In this embodiment of the invention, the nucleic acid encodes an amino acid sequence of 560 amino acid residues identified as SEQ ID No.: 10. In a preferred embodiment, the nucleotide sequence includes 2194 nucleotides of the human EAAT5 cDNA comprising 1680 nucleotides of coding sequence, 188 nucleotides of 5' untranslated sequence and 326 nucleotides of 3' untranslated sequence, identified as SEQ ID No.: 9. A preferred embodiment of the EAAT5 transporter is the nucleotide sequence depicted in FIGS. 1A through 1C (SEQ ID No: 9).

In another aspect, the invention comprises a homogeneous composition of the 61 kilodalton (kD) mammalian EAAT5 transporter and derivatives thereof, said size being understood to be the size of the protein before any post-translational modifications thereof. The amino acid sequence of the EAAT5 transporter and derivatives thereof preferably is the amino acid sequence of the human EAAT5 transporter protein shown in FIGS. 1A through 1C (SEQ ID No: 10). EAAT5 protein molecules provided by the invention are understood to have substantially the same biological properties as the EAAT5 protein molecule encoded by the nucleotide sequence described herein. Also provided by the invention are cell membrane preparations, preferably mammalian and amphibian cell membrane preparations, comprising the EAAT5 protein of the invention.

This invention provides both nucleotide and amino acid probes derived from the sequences herein provided. This invention includes probes isolated from either cDNA or genomic DNA, as well as probes made synthetically with the sequence information derived therefrom. The invention specifically included but is no limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent if expression of this transporter gene in various tissues of mammals, including human. It is also an object of the present invention to provide nucleic acid hybridization probes derived from the sequences of the excitatory amino acid transporter gene of the invention to be used for the detection and diagnosis of genetic diseases. It is an object of this invention to provide nucleic acid hybridization probes derived from the DNA sequence of the excitatory amino acid transporter gene herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be uses as antigens for the production of excitatory amino acid transporter-specific antibodies, or used for competitors of excitatory amino acid transporter molecules for amino acid, agonist, antagonist or drug binding, or to be used for the production of inhibitors of the binding of agonist or antagonists or analogues thereof to such excitatory amino acid transporter molecules.

The present invention also provides antibodies against and epitopes of the mammalian amino acid transporter molecules of the invention. It is an object of the present invention to provide antibodies that are immunologically reactive to the excitatory amino acid transporters of the invention. It is a particular object to provide monoclonal antibodies against this excitatory amino acid transporter, most preferably the human excitatory amino acid transporter as herein disclosed. Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with a cell line which expresses antigens or epitopes of an excitatory amino acid transporter of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the excitatory amino acid transporter of the invention. Chimeric antibodies immunologically reactive against the excitatory amino acid transporter protein of the invention are also within the scope of this invention.

The present invention provides recombinant expression constructs comprising a nucleic acid encoding an excitatory amino acid transporter of the invention wherein the construct is capable of expressing the encoded excitatory amino acid transporter in cells, preferably mammalian or amphibian cells, and most preferably in mammalian cell culture transformed with the construct or amphibian oocytes comprising excitatory amino acid-encoding mRNA. Preferred embodiments of such constructs comprise a cDNA encoding a mammalian EAAT5 protein having an amino acid sequence identified as SEQ ID No.: 10. In other preferred embodiments, the cDNA encodes human EAAT5, most preferably having a nucleic acid sequence identified as SEQ ID No.: 9. The recombinant expression constructs provided by the invention are capable of expressing the excitatory amino acid transporter encoded therein in cells and oocytes transformed with the construct or into which the construct has otherwise been introduced.

The invention also provides cultures cells transformed with the recombinant expression constructs of the invention, each such cultures being capable of and expressing the excitatory amino acid transporter encoded in the transforming construct. The invention also provides amphibian oocytes into which a recombinant expression construct of the invention is introduced, each such oocyte being capable of and expressing the excitatory amino acid transporter encoded in the transforming construct, or wherein RNA, most preferably mRNA, encoding the excitatory amino acid transporter protein has been introduced.

The present invention also includes within its scope protein preparations of prokaryotic and eukaryotic cell membranes containing the amino acid transporter protein of the invention, derived from cultures of prokaryotic or eukaryotic cells, respectively, transformed with the recombinant expression constructs of the invention. In a preferred embodiment, such preparation of cell membranes comprise the excitatory amino acid transporters protein of the invention.

The invention also provides methods for screening compounds for their ability to inhibit, facilitate or modulate the biochemical activity of the excitatory amino acid transporter molecules of the invention, for use in the in vitro screening of novel agonist and antagonist compounds. In preferred embodiments, cells, particularly amphibian oocytes comprising nucleic acid encoding a mammalian excitatory amino acid transporter protein of the invention, including recombinant expression constructs of the invention, are contacted with such a compound, and the effect of the compound on the excitatory amino acid transport is assayed. In preferred embodiments, transported amino acids include glutamate and aspartate, most preferably L-glutamate. Additional preferred embodiments comprise quantitative analyses of such effects. Also provided are assays that distinguish between the effects of such compounds on excitatory amino acid transport from effects of such compounds on chloride ion transport by the excitatory amino acid transporters of the invention The present invention is also useful for the detection of analogues, agonists or antagonists, heretofore known or unknown, of the excitatory amino acid transporters of the invention, either naturally occurring or embodied as a drug. In preferred embodiments, such analogues, agonists or antagonists may be detected in blood, saliva, semen, cerebrospinal fluid, plasma, lymph, vitreous humor, or any other bodily fluid. In additional preferred embodiments, the invention provides methods for detecting and identifying analogues, agonists or antagonists that preferentially affect either the amino acid uptake function or the chloride ion channel function of the amino acid transporters of the invention.

Specific preferred embodiments of the present invention will become evident from the following more detailed description of certain preferred embodiments and the claims.

DESCRIPTION OF THE DRAWINGS

FIGS. 1A through 1C illustrate the nucleotide (SEQ ID No.: 9) and amino acid (SEQ ID No.: 10) sequence of the human EAAT5 excitatory amino acid transporter.

FIG. 2 presents an amino acid sequence comparison between human EAAT5 (SEQ ID No.: 10) and the excitatory amino acid transporters EAAT1 (SEQ ID No.: 2), EAAT2 (SEQ ID No.: 4), EAAT3 (SEQ ID No.: 6) and EAAT4 (SEQ ID No.: 8), wherein amino acid residues identical in 4 of 5 transporters are shown in white-on-black lettering. Also shown is one potential version of the transmembrane topology of the transporters, where (i-o) indicates that the sequence segment is arrayed from the inside to the outside of the cell, and (o-i) indicates that the sequence segment is arrayed from the outside to the inside of the cell across the cell membrane. Eight transmembrane segments (termed I through VIII) are shown.

FIG. 4A shows the amount of ($^3$H)-glutamate uptake in oocytes voltage-clamped at −60mV (−60) or +10mV (+10) in normal Ringers solution (normal), sodium-free (0 Na$^+$) or chloride-free (0 Cl$^-$) Ringers solution, or in the presence of threo-β-hydroxyaspartate (THA) or L-trans-pyrollidine-2,4-dicarboxylic acid (tPDC), or uninjected (uninjected).

FIG. 4B is a graph of the L-glutamate dose- and voltage-dependent steady-state current elicited by application of L-glutamate to EAAT5-expressing oocytes (data averaged from 7 cells). L-glutamate was applied in the following concentrations: -□-=3 μM; -○-=10 μM; -△-=30 μM; -▽-100 μM; -◇-=300 μM; -x-=1000 μM. Figure FIG. 4C is a graph of the steady-state current elicited by application of 100 μM L-glutamate alone to Xenopus oocytes expressing human EAAT5 (shown as -□-) or in the presence of 100 μM tPDC (-△-), showing that tPDC blocks the L-glutamate induced steady state current. Application of 100 μm tPDC alone (-○-) elicited a small, outward current at hyperpolarized potentials.

FIG. 4D is a graph of the steady-state current elicited by application of 100 μM L-glutamate alone to Xenopus oocytes expressing human EAAT5 (shown as -□-) or in the presence of 100 μM THA (-△-), showing that THA blocks the L-glutamate induced steady state current. Application of 100 μm THA alone (-○-) elicited a small, outward current at hyperpolarized potentials.

FIG. 5A is a graph of the steady-state current elicited by application of 100 μM L-glutamate alone to Xenopus oocytes expressing human EAAT5 in normal Ringers solution (shown as -○-) or in Ringers solution where sodium ions have been replaced by N-methyl D-glucamine (-□-), showing that this replacement abolishes the L-glutamine induced current.

FIG. 5B is a graph of the steady-state current elicited by application of 100 μM L-glutamate alone to Xenopus oocytes expressing human EAAT5 in normal Ringers solution (shown as -○-) or in Ringers solution where chloride ions have been replaced by gluconate (-□-), showing that this replacement has no effect at negative potentials but blocks outward current at positive potentials.

FIG. 5C is a graph of the steady-state current elicited by application of 100 μM L-glutamate alone to undialyzed Xenopus oocytes expressing human EAAT5 (shown as -○-) or in oocytes having been dialyzed in chloride-free solution for >48 hours (-□-), showing that this replacement abolishes the L-glutamine induced current.

FIG. 5D is a graph of the steady-state current elicited by application of 100 μM L-glutamate alone to Xenopus oocytes expressing human EAAT5 in normal Ringers solution (shown as -○-) or in Ringers solution where chloride ions have been replaced by nitrate (-□-), showing that this replacement elicits a large outward current.

DETAILED DESCRIPTION OF THE PREFERRED EMBODIMENTS

Figure 3:
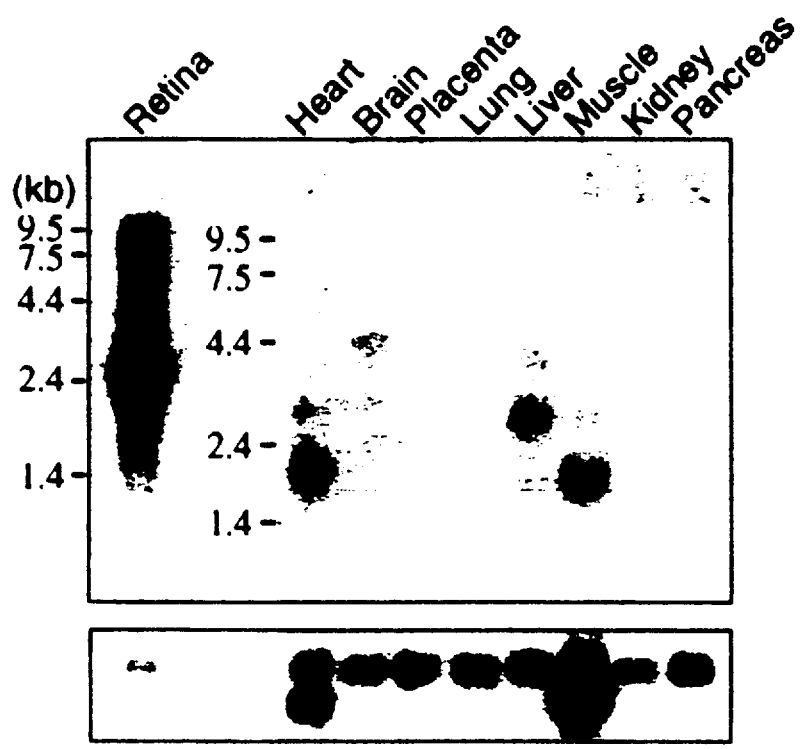
FIG. 3 is an autoradiograph of mRNA from retina and other tissues hybridized with a EAAT5 specific probe and illustrating retinal-specific expression of EAAT5 in human tissues. The bottom portion of the Figure shows the same filter stripped of EAAT5 probe and re-hybridized with a β-actin probe as a control for mRNA loading in each lane.

The term "excitatory amino acid transporter EAAT5" as used herein refers to protein having substantially the same biological activity as the protein having the amino acid sequence depicted in FIGS. 1A through 1C (SEQ ID No.: 10). This definition is intended to encompass allelic variations in the EAAT5 sequence and conservative amino acid substitution variants, either naturally occurring or the product of in vitro chemical or genetic modification, provided that the biochemical properties of the EAAT5 protein as disclosed herein are not substantially or materially affected. Each such variant will be understood to have essentially the same biochemical activity and amino acid sequence as the amino acid sequence of the corresponding EAAT5 protein disclosed herein.

The EAAT5 protein of the invention is encoded by an isolated nucleic acid, most preferably a nucleic acid sequence cloned into a replicable vector using vectors and methods known in the art. Cloned nucleic acid provided by the present invention may encode EAAT5 protein of any species of origin, including, for example, mouse, rat, rabbit, cat, and human, but preferably the nucleic acid provided by the invention encodes EAAT5 receptor of mammalian, most preferably human, origin.

The term "excitatory amino acid" is intended to encompass naturally-occurring and synthetic amino acids such as L-aspartate and L-glutamate, as well as homologues, analogues or derivatives thereof. The terms is also intended to encompass agonists, antagonist and inhibitors of mammalian glutamate and other excitatory amino acid transporters and receptors.

The term "detectably labeled" is intended to encompass any reporter molecule capable of being detected by radioactive, fluorescent, spectrophotometric or other physical or chemical means. Particular examples include radiolabels, including but not limited to $^3$H and $^{14}$C.

The term "chloride equilibrium potential" is intended to mean the membrane potential at which there is no detectable chloride ion flux across the cell membrane.

The nucleic acid hybridization probes provided by the invention comprise DNA or RNA having the nucleotide sequence of the amino acid transporters, depicted in FIGS. 1A through 1C (SEQ ID No.: 9), or any portion thereof effective in nucleic acid hybridization under stringency conditions sufficient to permit specific hybridization of the probe to a complementary nucleic acid sequence. Mixtures of such nucleic acid hybridization probes are also within the scope of this embodiment of the invention. Nucleic acid probes as provided herein are useful for detecting novel excitatory amino acid transporter genes related to the EAAT5 gene disclosed herein, specifically including homologous, cognate or syntenic transporter genes in non-human mammalian species. Nucleic acid probes as provided herein are also useful for detecting excitatory amino acid transporter gene expression in cells and tissues using techniques well-known in the art, including but not limited to Northern blot hybridization, in situ hybridization and Southern hybridization to reverse transcriptase—polymerase chain reaction (RT-PCR) product DNAs. The probes provided by the present invention, including oligonucleotides probes derived therefrom, are also useful for Southern hybridization of mammalian, preferably human, genomic DNA for screening restriction fragment length polymorphism (RFLP) associated with genetic disorders.

The production of proteins such as excitatory amino acid transporter molecules from cloned genes by genetic engineering means is well known in this art. This discussion which follows is accordingly intended as an overview of this field, and in not intended to reflect the full state of the art.

DNA encoding an excitatory amino acid transporter may be obtained, in view of the instant disclosure, by chemical synthesis, by screening reverse transcripts of mRNA from appropriate cells or cultured cell lines, by screening genomic libraries from appropriate cells or tissues, or by combinations of these procedures, as illustrated below. Screening of mRNA or genomic DNA may be carried out with oligonucleotide probes generated from the nucleic acid sequence information from the excitatory amino acid transporters disclosed herein. Probes may be labeled with a detectable group such as a fluorescent group, a radioactive atom or a chemiluminescent group in accordance with know procedures and used in conventional hybridization assays, as described. Nucleic acid sequences may be obtained by use of the polymerase chain reaction (PCR) procedure, using PCR oligonucleotide primers corresponding to nucleic acid sequence information derived from an excitatory amino acid transporter as provided herein. See U.S. Pat. Nos. 4,683,195 to Mullis et al. and 4,683,202 to Mullis.

The excitatory amino acid transporter protein of the invention may be synthesized in host cells transformed with a recombinant expression construct comprising a nucleic acid encoding excitatory amino acid transporter cDNA. Alternatively, the excitatory amino acid transporter proteins of the invention can be synthesized in amphibian oocytes comprising nucleic acid, preferably mRNA, encoding the excitatory amino acid transporter. Recombinant expression constructs provided by the invention can also be advantageously comprised of a vector that is a replicable DNA construct. Vectors are used herein either to amplify DNA encoding an excitatory amino acid transporter and/or to express DNA encoding an excitatory amino acid transporter gene. For the purposes of this invention, a recombinant expression construct is replicable DNA construct in which a nucleic acid encoding an excitatory amino acid transporter is operably linked to suitable control sequences capable of effecting the expression of the excitatory amino acid transporter in a suitable host or host cell.

The need for such control sequences will vary depending upon the host selected and the transformation method chosen. Generally, control sequences include a transcriptional promoter, optional ancillary transcription control sequences, such as transcription factor binding domains, enhancer sequences, and other eukaryotic "operator" sequences to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al.,: 1990, *Molecular Cloning: A Laboratory Manual* (Cold Spring Harbor Press: New York).

Vectors useful for practicing the present invention include plasmids, viruses (including phage), retroviruses, and integratible DNA fragments (i.e., fragments integratible into the host genome by homologous recombination). The vector replicates and functions independently of the host genome, or may, in some instances, integrate into the genome itself.

Suitable vectors will contain replicon and control sequences which are derived species compatible with the intended expression host. A preferred vector is pCMV5 (Andersson et al., 1989, *J Biol. Chem.* 264: 8222–8229). Transformed host cells are cells which have been transformed or transfected with recombinant expression constructs made using recombinant DNA techniques and comprising nucleic acid encoding an amino acid transporter protein. In addition, preferred vectors comprise control sequences for in vitro RNA synthesis, whereby RNA prepared in vitro is introduced into the appropriate host cell and excitatory amino acid transporter protein is produced thereby. Preferred host cells are *Xenopus laevis* oocytes, oocytes from other amphibian species, and COS-7 cells (Gluzman, 1981, *Cell* 23: 175–182). Transformed host cells may express the excitatory amino acid transporter protein, but host cells transformed for purposes of cloning or amplifying nucleic acid hybridization probe DNA need not express the transporter. When expressed, the excitatory amino acid transporter protein molecules of the invention will typically be located in the host cell membrane. See, Sambrook et al., *ibid.*

Cultures of cells derived from multicellular organisms are a desirable host for recombinant amino acid transporter protein synthesis. In principal, any higher eukaryotic cell culture is useful, whether from vertebrae or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. COS-7 cells are preferred.

Certain other primary host cells, not subjected to prolonged tissue culture adaptation, can be used to produce the amino acid transporter of the invention, particularly amphibian oocytes. Amphibian oocytes are useful for expressing the mammalian excitatory transporters of this invention, most preferably ooyctes from *Xenopus laevis* or other amphibian, which oocytes are used to provide cells convenient foe the practice of some of the inventive methods disclosed herein. In these embodiments, the nucleic acid encoding the excitatory amino acid transporter proteins of the invention is preferably RNA, more preferably mRNA, and most preferably in vitro synthesized mRNA as disclosed herein.

Thus, the invention also provides a method for making the mammalian excitatory amino acid transporters of the invention, most preferably human EAAT5, and membrane preparations comprising this transporter, by introducing nucleic acid encoding the transporter into an appropriate prokaryotic, or preferably, eukaryotic, most preferably mammalian, cell that is capable of expressing the transporter protein.

The invention provides homogeneous compositions of the EAAT5 proteins produced by transformed eukaryotic cells as provided herein. Such a homogeneous compositions are intended to be comprised of the corresponding excitatory amino acid transporter protein that comprises at least 50–90% of the protein in such a homogenous composition. The invention also provides membrane preparations from cells expressing the excitatory amino acid transporter protein as the result of transformation with a recombinant expression construct, as described herein.

Amino acid transporter protein made from closed genes in accordance with the present invention may be use for screening amino acid analogues, or inhibitors, agonists or antagonists of amino acid transport, or for determining the amount of such agonists or antagonists in a solution of interest (e.g. blood plasma or serum). For example, host cells may be transformed with a recombinant expression construct of the present invention, an excitatory amino acid transporter expressed in those host cells, and the cells or membranes thereof used to screen compounds for their effect on excitatory amino acid transport activity. By selection of host cells that do not ordinarily express an excitatory amino acid transporter, pure preparations of membranes containing the transporter can be obtained.

The recombinant expression constructs of the present invention are useful in molecular biology to transform cells which do not ordinarily express a excitatory amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, *Cell* 51: 503–512; Bertling, 1987, *Bioscience Reports* 7: 107–112; Smithies et al., 1985, *Nature* 317: 230–234.

In preferred embodiments, the electrochemistry of the EAAT5 proteins of the invention are analyzed, and analogues, agonists and antagonists assayed, using amphibian oocytes, most preferably *Xenopus laevis* oocytes, comprising a nucleic acid encoding the excitatory amino acid transporter proteins of the invention that is preferably RNA, more preferably mRNA, and most preferably in vitro synthesized mRNA as disclosed herein, wherein the excitatory amino acid transporter protein of the invention are expressed thereby in the cell membranes of the oocytes. Preferred electrochemical assays are performed as disclosed herein in the Examples set out below.

Oligonucleotides of the present invention are useful as diagnostic tools for probing excitatory amino acid transporter gene expression in tissues of humans and other animals. For example, tissues are probed in situ with oligonucleotide probes carrying detectable groups by conventional autoradiographic techniques, to investigate native expression of this transporter or pathological conditions related thereto.

The invention also provides antibodies that are immunologically reactive to the excitatory amino acid transporter protein or epitopes thereof provided by the invention. The antibodies provided by the invention may be raised, using methods well known in the art, in animals by inoculation with cells that express an excitatory amino acid transporter of the invention or epitopes thereof, cell membranes from such cells, whether crude membrane preparations or membranes purified using methods well known in the art, or purified preparations of proteins, including fusion proteins, particularly fusion proteins comprising epitopes of the excitatory amino acid transporter protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamster, goats and primates. Preferred animals for inoculation are rodents (including mice, rats, hamsters) and rabbits. The most preferred animal is the mouse.

Cells that can be used for such inoculations, or for any of the other means used in the invention, include any cell line that expresses the excitatory amino acid transporter protein of the invention, or any epitope thereof, as a result of a molecular or genetic engineering, or that has been treated to increase the expression of an endogenous or heterologous excitatory amino acid transporter protein by physical, biochemical or genetic means. Preferred cells are cells expressing the EAAT5 protein of the invention, including mammalian, insect and amphibian cells, and most preferably cells syngeneic to the animal to be inoculated, that have been transformed with a recombinant expression construct of the invention encoding an excitatory amino acid transporter protein, and that express the transporter therefrom.

The present invention also provides monoclonal antibodies that are immunologically reactive with an epitope derived from an excitatory amino acid transporter of the invention, or fragment thereof, present on the surface of such cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cell of a myeloma cell line with spleen cells derived from animals immunized with cells expressing an excitatory amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line in P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an excitatory amino acid transporter of the invention. The present invention also encompasses fragments, including but not limited to F(ab), F(ab)' and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an excitatory amino acid transporter of the invention, made by methods known to those of skill in the art.

The present invention also encompasses an epitope of an excitatory amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an excitatory amino acid transporter-derived epitope. The chimeric antibodies embodied in the present invention include those that are derived from naturally occurring antibodies as well as chimeric antibodies made by means of genetic engineering technology well known to those of skill in the art.

The invention also provides methods for screening compound for their ability to inhibit, facilitate or modulate the biochemical activity of the excitatory amino acid transporter molecules of the invention, for use in the in vitro screening of novel agonist and antagonist compounds. In preferred embodiments, cells, particularly amphibian oocytes transformed with a recombinant expression construct of the invention are contacted with such a compound, and the effect of the compound on the transport of the appropriate amino acid is assayed. Additional preferred embodiments comprise quantitative analyses of such effects. Also provided are assays that distinguish between the effect of such compounds on excitatory amino acid transport from effects of such compounds on chloride ion transport by the transporters of the invention.

As provided by the invention, such assays comprise a cell, most preferably a mammalian cell comprising a recombinant expression construct of the invention and expressing the excitatory amino acid transporter protein of the invention thereby, or an amphibian oocyte comprising a nucleic acid encoding an excitatory amino acid transporter protein of the invention and expressing said transporter thereby. In the practice of the methods of the invention, transporter activity is assayed using detectably-labeled excitatory amino acids or analogues thereof. In alternative embodiments, the electrophysiological and electrochemical effect of contacting such cells with an excitatory amino acid are assayed. Comparative assays performed in the presence or absence of putative analogues, agonists, antagonists, inhibitors, facilitators or modulators of transporter activity are provided by the invention.

The present invention is also useful for the detection of inhibitors, analogues, agonists or antagonists, heretofore known or unknown, of the excitatory amino acid transporters of the invention, either naturally occurring or embodied as a drug. In preferred embodiments, such inhibitors, analogues, agonists or antagonists may be detected in blood, saliva, semen, cerebrospinal fluid, plasma, lymph, or any other bodily fluid. In additional preferred embodiment, the invention provides methods for detecting and identifying inhibitors, analogues, agonists or antagonists that preferentially affect either the amino acid uptake function or the chloride ion channel function of the amino acid transporters of the invention.

In the practice of these embodiments of the invention, such assays comprise a cell or cell membrane, most preferably a mammalian cell comprising a recombinant expression construct of the invention and expressing the excitatory amino acid transporter protein of the invention thereby, or an amphibian oocyte comprising a nucleic acid encoding an excitatory amino acid transporter protein of the invention and expressing said transporter thereby. In the practice of the methods of the invention, transporter binding and activity are assayed using detectably-labeled excitatory amino acids or analogues thereof. In particular, the capacity for a mammalian sample comprising a fluid to compete with or inhibit binding of detectably-labeled excitatory amino acids or analogues thereof is assayed to detect the presence of inhibiting, modulating or competing compounds in a biological sample. Additionally, such assays are directed towards the effect of a biological sample comprising a fluid on the electrophysiological and electrochemical activity of excitatory amino acid transporter in response to the addition of an excitatory amino acid transporter substrate. Comparative assays performed in the presence or absence of the biological sample or appropriate dilutions thereof are also provided by the invention.

The Examples which follow are illustrative of specific embodiments of the invention, and various uses thereof. They set forth for explanatory purposes only, and are not to be taken as limiting the invention.

EXAMPLE 1

Isolation of a Human Excitatory Amino Acid Transporter c DNA

Excitatory amino acid transporters EAAT1, EAAT2 and EAAT3 have been disclosed in co-owned and co-pending U.S. Ser. No. 08/140,729, filed Oct. 20, 1993, now U.S. Pat. No. 5,658,782, issued Aug. 10, 1997, which is incorporated by reference herein in its entirety. Excitatory amino acid transporter EAAT4 has been disclosed in co-owned and co-pending U.S. Ser. No. 08/663,808, filed Jun. 14, 1996, which is incorporated by reference herein in its entirety.

A novel human excitatory amino acid transporter was cloned from retinal tissues using well-established techniques (see Sambrook et al., 1990, *Molecular Cloning: A Laboratory Manual* (Cold Springs Harbor Press: New York). Briefly, cDNA was prepared from human retinal mRNA and screened under conditions of reduced stringency with a glutamate transporter cDNA obtained from salamander retina. Plaque filter lifts from a λgt10 library of human retinal cDNA were hybridized overnight at 55° C. in a solution of 0.5M dibasic sodium phosphate, pH 7.5, 7% sodium dodecyl sulfate (SDS), 1mM ethylenediamine tetraacetic acid (EDTA) and salamander cDNA $^{32}$P-radiolabeled by random priming at $10^6$ cpm/mL. After hybridization, filters were washed at 55° C. on 2X standard saline phosphate/EDTA (SSPE, composed of 0.3M NaCl, 0.02M dibasic sodium phosphate, pH 7.4 and 2mM EDTA) and 1% SDS. Eight positively-hybridizing clones were isolated, and insert cDNA from these clones was separated from the λgt10 cloning vector by restriction enzyme digestion with EcoRI, subcloned into the plasmid pBSKII (obtained from Stratagene, LaJolla, Calif.) and characterized. The nucleotide sequence of two of these clones was determined for both DNA strands using a polymerase chain reaction-based sequencing system (PRISM, Applied Biosystems, Foster City, Calif.) and an automated DNA sequencer (Applied Biosystems Model 373 Stretch DNA Sequencer, Applied Biosystems). Sequence data analysis was performed using MacVector analysis software (IBI, New Haven, Conn.).

A portion of the nucleotide sequence of one of these clones, termed EAAT5, is shown in FIGS. 1A through 1C (SEQ ID No.: 9). This clone was 2.9 kilobases (kb) in length and was found to comprise 180 basepairs (bp) of 5' untranslated sequence containing two in-frame translation stop codons upstream (5') from a consensus Kozak sequence providing a translation initiation codon (ACCATGG). The clone contains an open reading frame following this translation initiation codon of 1683 bp, followed by approximately 1.1 kb of 3' untranslated sequence, 326 bp of which is shown in FIG. 1C. Analysis of the other clone, which was about 3.1 kb in length, suggested that the retinal tissue mRNA corresponding to EAAT5 was about 3.1 kb in length.

The predicted gene product of EAAT5 is 560 amino acids in length (SEQ ID No.: 10) and has a predicted molecular weight (prior to any post-translational modifications) of about 61 kilodaltons. A comparison of the EAAT5 amino acid sequence with the other EAAT subtypes is shown in FIG. 2, and indicates that EAAT5 is a related but distinct member of the family of EAAT subtypes. For example, the EAAT5 sequence contains a single N-linked glycosylation site (NXS/T) in a putative large extracellular loop, while EAAT1 through 3 contain 2 such sites and EAAT4 contains 3. Using optimal sequence alignment, EAAT5 has 46% sequence identity with EAAT1, 43% sequence identity with EAAT4, 37% sequence identity with EAAT3 and 36% sequence identity with EAAT2. (For comparison, EAAT1 has 52% sequence identity with EAAT4 and 49% with EAAT3, as disclosed in U.S. Pat. No. 5,658,782 and U.S. Ser. No. 08/663,808). The most striking sequence conservation observed between these different subtypes is found in a large hydrophobic sequence that includes the sequence AAIFIAQ (residues 388–394 in EAAT5). However, both the amino and carboxyl termini of these proteins, which are believed to be topographically arranged intracellularly, are poorly conserved. Notably, the amino acid sequence of the carboxyl terminus of EAAT5 conform to a sequence motif found in synaptic membrane proteins: E—(S/T)—X—V—COOH (see Sheng, 1996, *Neuron* 17: 575–578 for review). Table I provides a comparison of the EAAT5 carboxyl terminal amino acid sequence with those of the NMDA receptor subunits NR2A and NR2B and the Shaker-type potassium channel Kv1.4:

TABLE I

| Protein | C-terminal sequence |
|---------|---------------------|
| EAAT5   | S-E-L-E-T-N-V       |
| NR2A    | P-S-I-E-S-D-V       |
| NR2B    | S-S-I-E-S-D-V       |
| Kv1.4   | K-A-V-E-T-D-V       |

In these other proteins, interactions with a post-synaptic specific protein, postsynaptic density protein-95 (PSD-95), and particularly with certain domains of this protein (termed PDZ modular protein binding domains) have been studied, and the sequence similarity in EAAT5 indicates that EAAT5 should also interact with PSD-95. Preliminary results using a yeast two hybrid assay for protein-protein interactions indicate that EAAT5 has the ability to interact with PSD-95.

These results indicate that EAAT5 is a novel member of the excitatory amino acid transporter gene family that is expressed in retina.

EXAMPLE 2
Tissue Distribution of EAAT5 Expression

The tissue distribution of mRNA expression of the EAAT5 gene disclosed herein was determined in various tissues by Northern hybridization analysis (see Sambrook et al., *ibid.*) using human EAAT5 as a hybridization probe. The results of these experiments are shown in FIG. 3.

Human retinal poly(A)$^+$ RNA (2 $\mu$g) was size-fractionated by denaturing formaldehyde agarose gel electrophoresis and transferred to a nylon membrane (Sambrook et al., *ibid.*). This membrane and Multiple Tissue Northern Blot (Clonetech, Palo Alto, Calif.) were hybridized with human EAAT5 coding sequence that had been radiolabeled with $^{32}$P-dCTP (New England Nuclear, Boston, Mass.) by random priming (using a kit obtained from Boehringer Mannheim, Indianapolis, Ind.). Filters were hybridized overnight at 42° C. in a solution of 5X SSPE, 50% formamide, 7.5% Denhardt's solution, 2% SDS, 100 $\mu$g/mL denatured salmon sperm DNA and 10$^6$ cpm/mL radiolabeled probe. Hybridization was visualized by autoradiography following two 30-min room temperature washes of the hybridized membranes in 2X SSPE/0.1% SDS followed by two 20-min washes at 50° C. in 0.1X SSPE/0.1% SDS. After autoradiography thee membranes were stripped and re-hybridized with a radiolabeled P-actin probe to provide a control for RNA loading variations in each size-fractionated RNA sample.

These Northern blot analyses shown in FIG. 3 indicate that a 3.1kb mRNA species encoding EAAT5 is abundantly expressed in human retina. A band of about the same size is also detected in liver, but at expression levels at least 20-fold lower than in retina. Weak hybridizing bands of about 2kb in size were also detected in heart and muscle, and a very light band of approximately 4.5kb was seen in brain RNA. It was not determined whether these differently sized bands reflect differential processing of the EAAT5 gene in these tissues or cross-hybridization of the EAAT5 probe with a closely related gene. However, these RNA sizes do not correspond to any of the other known EAAT subtypes. In order to determine whether the weak hybridization in brain RNA reflected a restricted distribution in certain brain regions, 20$\mu$g of total RNA isolated from six different human brain regions (frontal and motor cortex, hippocampus, thalamus, basal ganglia, and cerebellum) were assayed by Northern hybridization as described above. No hybridization signal was detected in these experiments.

These results strongly suggest that EAAT5 expression is retina-specific.

EXAMPLE 3
Functional Expression of EAAT5 in Xenopus Oocytes

The sequence similarity between EAAT5 as disclosed herein and the previously-identified glutamate transporters EAAT1 through EAAT4 suggested that the EAAT5 protein was also an excitatory amino acid transporter. The biochemical and electrochemical activity of the EAAT5 protein was assayed in Xenopus oocytes following microinjection of in vitro synthesized EAAT5-encoding RNA.

Briefly, the coding sequence of the EAAT5 cDNA shown in FIGS. 1A through 1C (SEQ ID No.: 9) was isolated with unique flanking restriction endonuclease recognition sites using a polymerase chain reaction (PCR)-based technique. In this method, each of the complementary primers used for PCR amplification of the EAAT5 coding sequence contained a sequence encoding a unique restriction endonuclease recognition site. The sense primer contained a recognition site for restriction enzyme Asp718, and the antisense primer contained a recognition site for XbaI. The complete sequence of each PCR primer used for this amplification reaction are:

EAAT5 sense primer:

CGCCGGTACCTCACCATGGTGCCGCAT    (SEQ ID No.: 13);
EAAT5 antisense primer:

CGCCTCTAGAGGCTCAGACATTGGTCTC    (SEQ ID No.: 14).

PCR amplification was performed for 25 cycles, each cycle comprising 30 seconds at 94° C. (denaturation), 30 seconds at 55° C. (annealing) and 2 minutes at 72° C. (extension) in 100 μL reaction mixture containing 1 μM each oligonucleotide primer, 10 ng plasmid template cDNA, 300 μM each deoxynucleotide, reaction buffer and Vent polymerase (New England Biolabs, Needham, Mass.). Following PCR amplification, the product of the reaction was purified using standard techniques (see Saiki et al., 1988, *Science* 239: 487–491) and the amplified DNA digested with Asp718 and XbaI. The digested amplified DNA was then subcloned into plasmid pOTV (see Arriza et al., ibid.) for preparing RNA for expression experiments in Xenopus oocytes.

EAAT5 RNA was prepared as follows. pOTV plasmid comprising the subcloned EAAT5 amplified cDNA as described was digested with restriction endonuclease SpeI and synthetic RNA transcribed using T7 RNA polymerase and a mMessage mMachine RNA capping kit (Ambion, Austin, Tex.). EAAT5 mRNA so prepared was then dilute with water to a concentration of 400 μg/mL, and 50 nL of this EAAT5 mRNA was then microinjected into defolliculated stage V–VI *Xenopus laevis* oocytes. Oocytes were prepared as described (Quick & Lester, 1994, *Methods in Neuroscience* 19: 261–279) and used for expression experiments 2–5 days later.

Radiolabeled glutamate uptake experiments were performed at room temperature under voltage clamp at −60 mV (except, where noted, at +10 mV). Currents were recorded during bath application of 100 μM ($^3$H)-L-glutamate (obtained from New England Nuclear, Boston, Mass.) in Ringers solution (96 mM NaCl, 2 mM KCl, 1.8 mM $CaCl_2$, 1 mM $MgCl_2$, and 5 mM HEPES, pH 7.5) ) for 100 seconds, the tritiated L-glutamate having a specific activity of 20 Ci/mmol. After 100 second incubation in the presence of tritiated substrate, oocytes were washed in the bath for 3 minutes to reduce background radioactivity, and then individually lysed for >15 minutes in a scintillation vial containing 1% SDS. After cell lysis, scintillation cocktail was added to each vial and the amount of radioactivity counted.

Figure 4A:
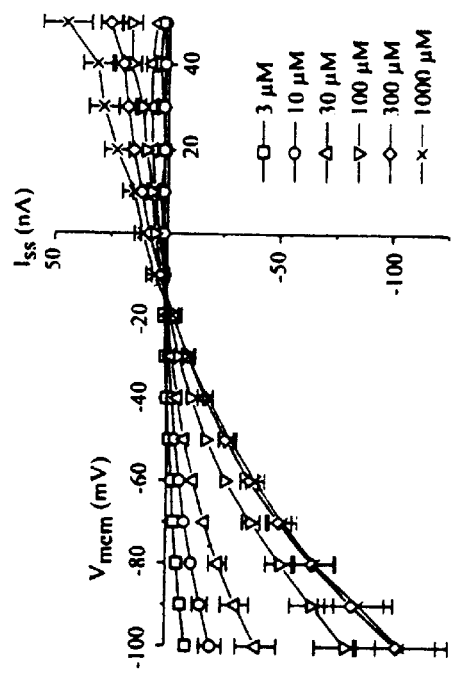
FIGS. 4A through 4D illustrate the results of functional assays performed using *Xenopus laevis* oocytes injected with and expressing EAAT5 mRNA.

The results of these experiments are shown in FIG. 4A. Uptake of radiolabeled glutamate was significantly increased over uninjected oocytes (typically 2- to 10-fold); however, this was less of a difference when comparing the amount of radiolabeled glutamate uptake in cells expressing EAAT-1, -2 or -3 (which was typically 50-fold; see U.S. Pat. No. 5,658,782). EAAT5 glutamate uptake was found to be both sodium- and voltage dependent, as evidenced by comparison of the amount of radiolabeled glutamate uptake in the absence of sodium (by replacement of sodium ions by N-methyl glucamine, represented in the Figure as "0 $Na^+$") and by the difference in radiolabeled glutamate uptake in voltage clamped experiments performed at +10 mV (represented by "+10" in the Figure). EAAT5 was similar to all other known EAAT subtypes in that glutamate uptake was not significantly affected by replacing external chloride ion with gluconate.

Two electrode voltage clamp recordings from EAAT5 expressing oocytes were performed at room temperature using glass microelectrodes filled with 3M KCl solution (resistance <1MΩ) and a Ag/AgCl pellet bath ground or an active bath probe. An Axon GeneClamp 500 amplifier was used with Digidata 1200 interfaces and controlled using pClamp6 software (Axon Instruments, Foster City, Calif.). Steady state currents were filtered at 2 kHz and digitized at 5 kHz. For current-voltage curves, the oocyte membrane potential was held at −30 mV and stepped through a range of +50 to −100 in 100 millisecond steps. Steady state currents were measured during the final 20 milliseconds of the command step.

The results of these experiments are shown in FIG. 3B. Application of glutamate to oocytes expressing EAAT5 generated a current that was both voltage and concentration dependent. The current was found to reverse at −20±1 mV, and this reversal potential was not affected by the glutamate concentration. Although nor predicted for an EAAT transporter, a outward current was observed that was similar to the outward current observed in oocytes expressing the EAAT4 transporter (as disclosed in co-owned and co-pending U.S. Ser. No. 08/663,808). Currents were also elicited by L- and D-aspartate and, much less potently, by D-glutamate. The apparent affinity ($EC_{50}$) and maximum current ($I_{max}$) for these compounds at a membrane potential held at −60 mV is shown in Table II:

TABLE II

| Compound | n | $EC_{50}$, μM | $I_{max}$ |
|---|---|---|---|
| L-glutamate | 5 | 64 ± 6 | (1) |
| D-glutamate | 4 | >10,000 | (0.21 ± 0.06) |
| t-aspartate | 5 | 13 ± 5 | 0.67 ± 0.20 |
| D-aspartate | 4 | 64 ± 10 | 0.72 ± 0.03 |
| THA | 6 | 1.0 ± 0.1 | (0) |
| tPDC | 4 | 6.2 ± 1.7 | (0) | where $I_{max}$ is normalized to L-glutamate $I_{max}$ in the same oocyte. L-trans-pyrollidine-2,4-dicarboxylic acid (THA) and threo-β-hydroxyaspartate (tPDC) did not induce currents in these oocytes. EAAT5 exhibits considerable stereospecificity for L-glutamate over D-glutamate, and a slight preference for L-aspartate over D-aspartate, and the affinity for L-glutamate is modestly voltage-dependent, increasing e-fold per 86 mV.

Figure 4C:
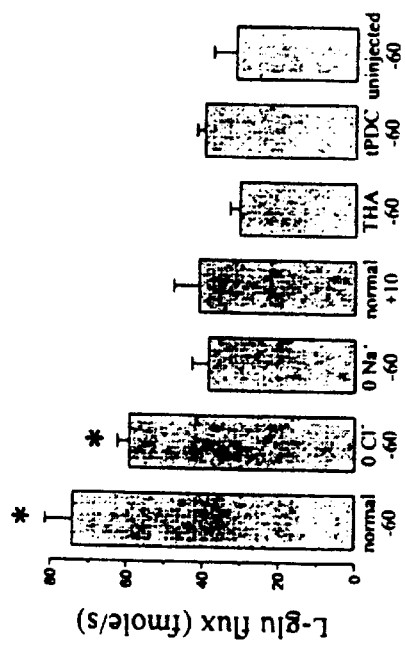
Figure 4B:
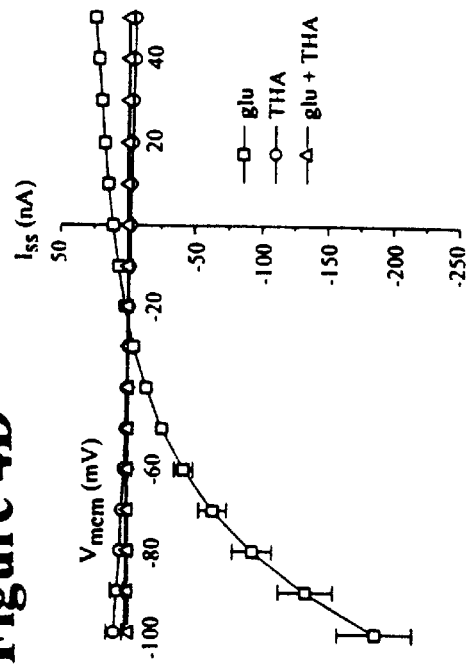
Figure 4D:
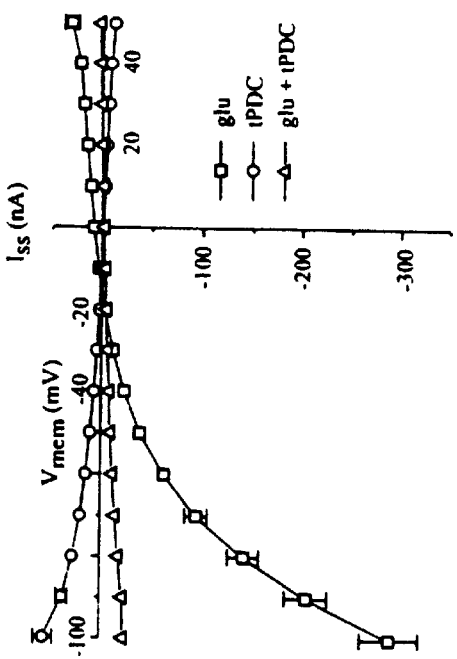

Both THA and tPDC were found to be potent blockers of both glutamate uptake (shown in FIG. 4A) and in the glutamate-elicited current in EAAT5-expressing oocytes. These results are shown in FIGS. 4C and 4D. Co-application of either 100 μM THA or 100 μM tPDC with glutamate almost entirely abolished the elicited current, as shown in these Figures. Neither compound generated a current with a voltage dependence similar to that of glutamate, even though these compounds acted as competitive substrates of other EAAT subtypes. In fact, both compounds applied to EAAT5-expressing oocytes alone elicited outward currents at negative potentials which became small and inward at positive potentials. In contrast, the high affinity EAAT2 subtype blocker kainate had minimal effect on EAAT5 function: in five cells tested, 1 mM kainate reduced the response to 100 μM glutamate to 84±11% of control over the range of −100 to −40 mV.

Figure 5B:
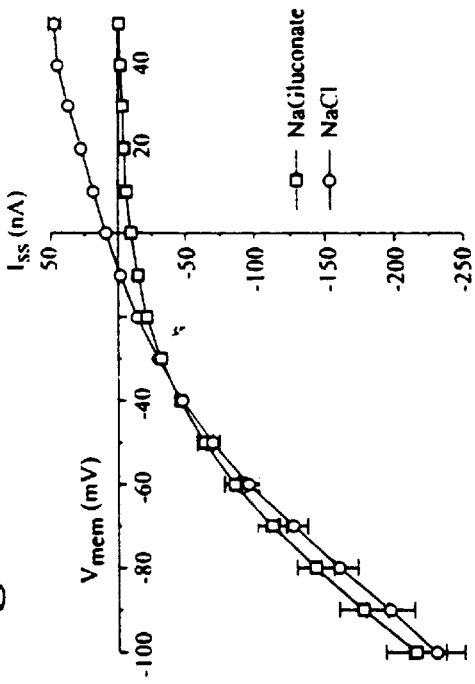
FIGS. 5A through 5D illustrate the ion dependence of EAAT5 mediated currents induced in Xenopus oocytes expressing human EAAT5.
Figure 5D:
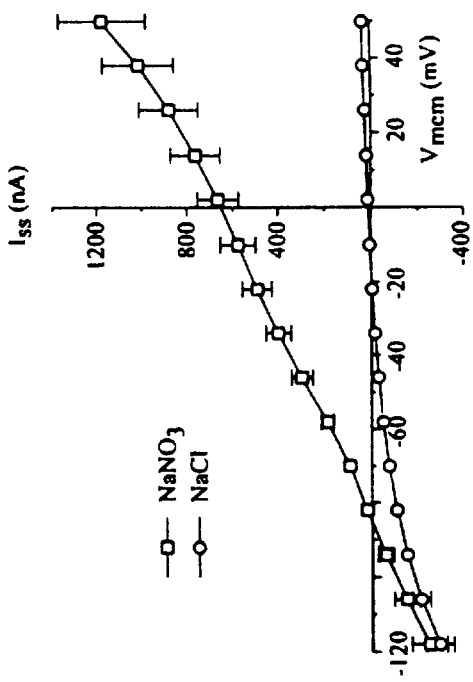
Figure 5A:
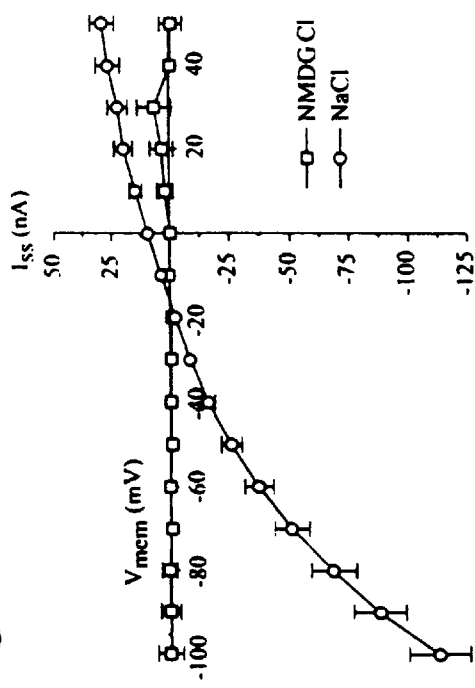
Figure 5C:
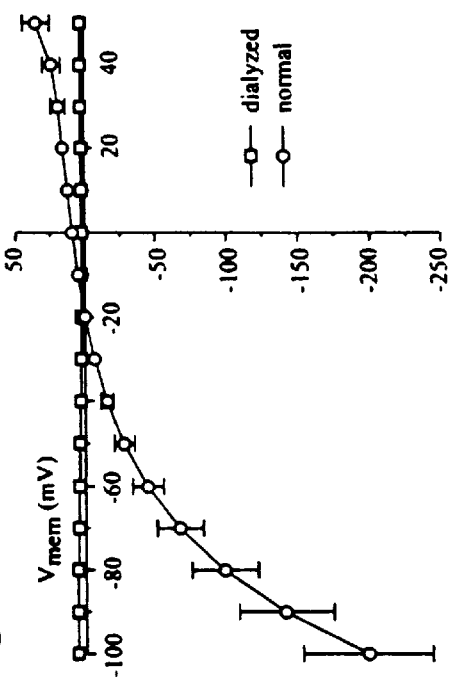

The dependence of EAAT5 glutamate-elicited currents on sodium and chloride ions is shown in FIGS. 5A through 5D. Sodium ion dependence is illustrated in FIG. 5A, where glutamate-elicited current is abolished in experiments performed in Ringer's solution in which sodium ions are replaced with N-methyl glucamine. These results reflect the sodium ion dependence observed for radiolabeled glutamate uptake shown in FIG. 3A. Replacing chloride ion with gluconate ion, on the other hand, had no effect on steady state glutamate induced inward current but was observed to eliminate the outward current (FIG. 5B). This result suggested that at least a portion of the glutamate-induced outward current was the result of passive flux of chloride ions, consistent with the behavior of other EAAT subtypes. To further characterize this chloride ion dependence, oocytes were dialyzed in chloride-free media for at least 48 hours prior to voltage clamp experiments performed in the absence of external chloride ion; the results of these assays are shown in FIG. 5C. Dialysis was found to abolish glutamate-elicited current in all ten cells tested, while control oocytes showed the normal steady state current induced by application of 100 μM glutamine to EAAT5-expressing oocytes. In additional experiments, external chloride ion was replaced by nitrate (FIG. 5D): in these experiments, nitrate substantially increased the glutamate-elicited outward current due to the influx of the more permeant nitrate ion as external anion. These results are consistent with the observed behavior of other EAAT subtypes in voltage clamp experiments performed in the presence of 100 μM glutamate and external nitrate ion.

These results demonstrated that the EAAT5 protein of the receptor exhibits biochemical and electrochemical properties of an excitatory amino acid transporter. These results are also consistent with EAAT5 being involved with a glutamate-gated chloride conductance associated with both presynaptic and postsynaptic aspects of the retinal light response. The human EAAT5 protein disclosed herein exhibits the ion-dependence and most of the pharmacological properties of retinal glutamate-related biochemical activities previously observed and unexplained in the art.

EXAMPLE 4
Construction of Fusion Proteins-Recombinant Expression Constructs for Expression of Immunologically-Active Epitopes of Amino Acid Transporters The EAAT5 amino acid transporter protein of the invention are expressed as fusion proteins in bacteria to produce immunologically-active epitopes. In these experiments, the amino acid transporters cDNAs of the invention are excised from their respective pOTV-containing constructs and subcloned into a pGEX-2T construct (Pharmacia, Piscataway, N.J.) whereby the coding sequences of the amino acid transporter cDNA is translationally in-frame with sequences encoding glutathione-S-transferase (described in Arriza et al., 1992, *J Neurosci* 12: 4045–4055), termed pGST-EAAT5 constructs. After introduction of the pGST-EAAT5 constructs into bacterial cells (*E. coli*, strain D5α) using conventional techniques (see Sambrook et al., *ibid*), fusion protein expression is induced with isopropyl-1-thio-β-D-galactopyranoside as described (Smith & Johnson, 1988, *Gene* 67: 31–40) and purified using glutathione-Sepharose 4B (Pharmacia). Antibodies are then raised against the amino acid transporter of the invention by inoculation of rabbits with 300–500 μg of purified fusion protein in Freund's adjuvant (Grand Island Biological C., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual,* Cold Spring Harbor Laboratory Press, Cold Spring Harbor, N.Y.).

It should be understood that the foregoing disclosure emphasized certain specific embodiments of the invention and that all modification or alternatives equivalent thereto are within the spirit and scope of the invention as set forth in the appended claims.

We claim:

1. An isolated nucleic acid encoding a human excitatory amino acid transporter that is the EAAT5 glutamate transporter.

2. A nucleic acid according to claim 1 wherein the mammalian excitatory amino acid transporter has an amino acid sequence identified as SEQ ID No.: 10.

3. A nucleic acid according to claim I having a nucleotide sequence identified as SEQ ID No.: 9.

4. A nucleic acid hybridization probe comprising the nucleotide sequence of claim 1.

5. A recombinant expression construct comprising a nucleic acid of claim 1.

6. A cell transformed with a recombinant expression construct according to claim 4.

7. An amphibian oocyte expressing a mammalian excitatory amino acid transporter according to claim 1.

8. The amphibian oocyte of claim 7 that is a *Xenopus laevis* oocyte.

9. The amphibian oocyte of claim 7 expressing a mammalian excitatory amino acid transporter according to claim 2.

10. An isolated nucleic acid encoding a human excitatory amino acid transporter that hybridizes to a nucleic acid probe identified by Seq. ID No.: 9 at a temperature of 42° C. in a solution of 5X SSPE, 50% formamide, 7.5% Denhardt's solution, 2% SDS, and 100 Fg/mL denatured salmon sperm DNA.

11. An isolated nucleic acid according to claim 10 wherein hybridization is detected after washing in a solution of 2X SSPE, 0.1% SDS at room temperature and in a solution of 0.1X SSPE, 0.1% SDS at 50° C.

* * * * *